(12) United States Patent
Doisneau et al.

(10) Patent No.: US 11,857,277 B2
(45) Date of Patent: Jan. 2, 2024

(54) ROBOTICALLY CONTROLLED CLOT MANIPULATION AND REMOVAL

(71) Applicant: Auris Health, Inc., Redwood City, CA (US)

(72) Inventors: Anne Donahue Doisneau, San Francisco, CA (US); Alexander Tarek Hassan, San Francisco, CA (US); Frederic H. Moll, San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 213 days.

(21) Appl. No.: 16/748,405

(22) Filed: Jan. 21, 2020

(65) Prior Publication Data

US 2020/0253670 A1    Aug. 13, 2020

Related U.S. Application Data

(60) Provisional application No. 62/803,328, filed on Feb. 8, 2019.

(51) Int. Cl.
*A61B 34/30*        (2016.01)
*A61B 17/22*        (2006.01)
(Continued)

(52) U.S. Cl.
CPC ........ *A61B 34/30* (2016.02); *A61B 17/12136* (2013.01); *A61B 17/3207* (2013.01);
(Continued)

(58) Field of Classification Search
CPC .... A61B 2034/303; A61B 2017/22067; A61B 2017/22079
See application file for complete search history.

(56) References Cited

U.S. PATENT DOCUMENTS

| 5,011,488 A | 4/1991 | Ginsburg |
| 5,199,417 A | 4/1993 | Muller et al. |

(Continued)

FOREIGN PATENT DOCUMENTS

| EP | 0 347 098 | 2/1996 |
| EP | 2737922 A1 | 6/2014 |

(Continued)

OTHER PUBLICATIONS

International search report and written opinion dated Mar. 11, 2020 in application No. PCT/US2020/014438.
(Continued)

*Primary Examiner* — Martin T Ton
(74) *Attorney, Agent, or Firm* — Conley Rose, P.C.; Gayatry S. Nair

(57) ABSTRACT

Certain aspects relate to systems, devices, and techniques for clot manipulation and removal. At least some of the devices for clot manipulation and removal can be robotically controlled. These devices can include one or more elongate members that can be robotically driven through a patient's vasculature. One such device can include a first elongate member that can serve as an access sheath, a second elongate member that can serve as a clot removal catheter, a third elongate member that can serve as a clot disruptor, and a fourth elongate member that can serve as a guidewire.

18 Claims, 35 Drawing Sheets

(51) Int. Cl.
*A61B 17/12* (2006.01)
*A61B 17/3207* (2006.01)
*A61B 90/00* (2016.01)

(52) U.S. Cl.
CPC ............ *A61B 2017/22038* (2013.01); *A61B 2034/301* (2016.02); *A61B 2034/303* (2016.02); *A61B 2090/08021* (2016.02)

(56) References Cited

U.S. PATENT DOCUMENTS

| | | | |
|---|---|---|---|
| 5,876,325 | A | 3/1999 | Mizuno et al. |
| 8,021,326 | B2 | 9/2011 | Moll et al. |
| 8,652,030 | B2 | 2/2014 | Matsuura et al. |
| 9,504,604 | B2 | 11/2016 | Alvarez |
| 9,561,083 | B2 | 2/2017 | Yu et al. |
| 9,622,827 | B2 | 4/2017 | Yu et al. |
| 9,636,184 | B2 | 5/2017 | Lee et al. |
| 9,668,768 | B2 | 6/2017 | Piron et al. |
| 9,713,509 | B2 | 7/2017 | Schuh et al. |
| 9,717,563 | B2 | 8/2017 | Tognaccini |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,782,229 | B2 | 10/2017 | Crawford |
| 9,788,910 | B2 | 10/2017 | Schuh |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,080,576 | B2 | 9/2018 | Romo et al. |
| 10,136,959 | B2 | 11/2018 | Mintz et al. |
| 10,145,747 | B1 | 12/2018 | Lin et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,383,765 | B2 | 8/2019 | Alvarez et al. |
| 10,398,518 | B2 | 9/2019 | Yu et al. |
| 10,405,939 | B2 | 9/2019 | Romo et al. |
| 10,405,940 | B2 | 9/2019 | Romo |
| 10,426,559 | B2 | 10/2019 | Graetzel et al. |
| 10,426,661 | B2 | 10/2019 | Kintz |
| 10,434,660 | B2 | 10/2019 | Meyer |
| 10,464,209 | B2 | 11/2019 | Ho et al. |
| 10,470,830 | B2 | 11/2019 | Hill |
| 10,482,599 | B2 | 11/2019 | Mintz et al. |
| 10,493,241 | B2 | 12/2019 | Jiang |
| 10,500,001 | B2 | 12/2019 | Yu et al. |
| 10,517,692 | B2 | 12/2019 | Eyre et al. |
| 10,524,866 | B2 | 1/2020 | Srinivasan |
| 10,539,478 | B2 | 1/2020 | Lin |
| 10,639,114 | B2 | 5/2020 | Schuh |
| 10,646,291 | B2 | 5/2020 | Turner |
| 10,765,487 | B2 | 9/2020 | Ho |
| 2002/0082612 | A1 | 6/2002 | Moll et al. |
| 2003/0181809 | A1 | 9/2003 | Hall et al. |
| 2004/0176751 | A1 | 9/2004 | Weitzner et al. |
| 2006/0058617 | A1 | 3/2006 | Sano et al. |
| 2006/0178556 | A1 | 8/2006 | Hasser et al. |
| 2007/0013336 | A1* | 1/2007 | Nowlin ................ A61B 34/35 318/568.21 |
| 2007/0197896 | A1* | 8/2007 | Moll .................. A61B 1/00039 600/407 |
| 2007/0299456 | A1* | 12/2007 | Teague ................ A61B 17/221 606/127 |
| 2008/0082109 | A1* | 4/2008 | Moll ...................... A61B 34/30 606/130 |
| 2008/0147089 | A1 | 6/2008 | Loh |
| 2009/0005768 | A1 | 1/2009 | Sharareh |
| 2009/0048611 | A1 | 2/2009 | Funda |
| 2009/0326318 | A1 | 12/2009 | Tognaccini |
| 2010/0100045 | A1 | 4/2010 | Pravongviengkham et al. |
| 2010/0234857 | A1 | 9/2010 | Itkowitz |
| 2011/0184241 | A1* | 7/2011 | Zubiate ................. B25J 9/104 600/141 |
| 2011/0277775 | A1 | 11/2011 | Holop et al. |
| 2012/0283747 | A1 | 11/2012 | Popovic |
| 2012/0302869 | A1 | 11/2012 | Koyrakh |
| 2013/0218005 | A1* | 8/2013 | Desai ..................... A61B 18/12 600/424 |
| 2014/0051049 | A1 | 2/2014 | Jarc |
| 2014/0142591 | A1 | 5/2014 | Alvarez et al. |
| 2014/0243801 | A1 | 8/2014 | Fanelli et al. |
| 2014/0276913 | A1* | 9/2014 | Tah ...................... A61B 17/221 606/114 |
| 2014/0357984 | A1 | 12/2014 | Wallace et al. |
| 2014/0364870 | A1 | 12/2014 | Alvarez et al. |
| 2015/0025549 | A1 | 1/2015 | Kilroy et al. |
| 2015/0045675 | A1 | 2/2015 | Chernomorsky |
| 2015/0088161 | A1 | 3/2015 | Hata |
| 2015/0164596 | A1 | 6/2015 | Romo |
| 2015/0223832 | A1 | 8/2015 | Swaney |
| 2015/0297299 | A1 | 10/2015 | Yeung |
| 2015/0305650 | A1 | 10/2015 | Hunter |
| 2016/0001038 | A1 | 1/2016 | Romo et al. |
| 2016/0270865 | A1 | 9/2016 | Landey et al. |
| 2016/0287279 | A1 | 10/2016 | Bovay et al. |
| 2017/0007337 | A1 | 1/2017 | Dan |
| 2017/0071456 | A1 | 3/2017 | Ratnakar |
| 2017/0095299 | A1 | 4/2017 | Hendrick |
| 2017/0119481 | A1 | 5/2017 | Romo et al. |
| 2017/0135710 | A1 | 5/2017 | Hasegawa et al. |
| 2017/0135833 | A1 | 5/2017 | Syed |
| 2017/0143442 | A1 | 5/2017 | Tesar |
| 2017/0165011 | A1 | 6/2017 | Bovay et al. |
| 2017/0189118 | A1 | 7/2017 | Chopra |
| 2017/0189131 | A1 | 7/2017 | Weir |
| 2017/0202627 | A1 | 7/2017 | Sramek et al. |
| 2017/0209073 | A1 | 7/2017 | Sramek et al. |
| 2017/0290631 | A1 | 10/2017 | Lee et al. |
| 2017/0340396 | A1 | 11/2017 | Romo et al. |
| 2017/0367782 | A1 | 12/2017 | Schuh et al. |
| 2018/0025666 | A1 | 1/2018 | Ho et al. |
| 2018/0098817 | A1 | 4/2018 | Nichogi et al. |
| 2018/0177556 | A1 | 6/2018 | Noonan et al. |
| 2018/0214011 | A1 | 8/2018 | Graetzel et al. |
| 2018/0221038 | A1 | 8/2018 | Noonan et al. |
| 2018/0221039 | A1 | 8/2018 | Shah |
| 2018/0250083 | A1 | 9/2018 | Schuh et al. |
| 2018/0271616 | A1 | 9/2018 | Schuh et al. |
| 2018/0279852 | A1 | 10/2018 | Rafil-Tari et al. |
| 2018/0280660 | A1 | 10/2018 | Landey et al. |
| 2018/0289431 | A1 | 10/2018 | Draper et al. |
| 2018/0325499 | A1 | 11/2018 | Landey et al. |
| 2018/0333044 | A1 | 11/2018 | Jenkins |
| 2018/0338799 | A1 | 11/2018 | Hladio et al. |
| 2018/0360435 | A1 | 12/2018 | Romo |
| 2018/0360479 | A1* | 12/2018 | Hofmann ........... A61M 25/0116 |
| 2018/0368920 | A1 | 12/2018 | Ummalaneni |
| 2019/0000559 | A1 | 1/2019 | Berman et al. |
| 2019/0000560 | A1 | 1/2019 | Berman et al. |
| 2019/0000576 | A1 | 1/2019 | Mintz et al. |
| 2019/0083183 | A1 | 3/2019 | Moll et al. |
| 2019/0110839 | A1 | 4/2019 | Rafii-Tari et al. |
| 2019/0110843 | A1 | 4/2019 | Ummalaneni et al. |
| 2019/0151148 | A1 | 4/2019 | Alvarez et al. |
| 2019/0167366 | A1 | 6/2019 | Ummalaneni |

(56) References Cited

U.S. PATENT DOCUMENTS

| | | |
|---|---|---|
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |

FOREIGN PATENT DOCUMENTS

| | | |
|---|---|---|
| EP | 3335647 A2 | 6/2018 |
| EP | 3417901 A1 | 12/2018 |
| WO | WO 17/048194 | 3/2017 |
| WO | WO-2019005992 A1 | 1/2019 |

OTHER PUBLICATIONS

Darwiche, 2015, Operative technique and early experience for robotic assisted laparoscopic nephroureterectomy (RALNU) using da Vinci XI, SpringerPlus, 4:298.

Sasaki, 2017, Laparoscopic hemicolectomy for a patient with situs inversus totalis: a case report, Int. J. Surg. Case Rep. 41:93-96.

\* cited by examiner

ROBOTICALLY CONTROLLED CLOT MANIPULATION AND REMOVAL

CROSS-REFERENCE TO RELATED APPLICATION(S)

This application claims the benefit of U.S. Provisional Application No. 62/803,328, filed Feb. 8, 2019, which is hereby incorporated by reference in its entirety.

TECHNICAL FIELD

The systems and methods disclosed herein are directed to medical systems, and more particularly to medical systems for robotically controlled clot manipulation and removal.

BACKGROUND

Blood clots are gel-like clumps of semi-solid mass that can form along vessels throughout a patient's vasculature. Clots can form anywhere in an individual's vasculature system, including but not limited to the cerebrovasculature, pulmonary arteries, or peripheral arteries.

Clotting can cause a number of problems, including stroke. For example, one of the most common types of stroke is an ischemic stroke, which occurs when arteries to the brain become narrowed or blocked due to blood clots, thereby causing severely reduced blood flow or ischemia. This type of stroke can often result in the rapid loss of neurons.

Accordingly, there is a need to provide improved systems, devices, and methods that can manipulate and remove clots in a safe and efficient manner.

SUMMARY

The systems, devices and methods described herein relate to the manipulation and removal of clots within a patient's vasculature.

In one aspect, a robotically controlled system for removing a clot from a patient includes an instrument system including a first elongate member and a second elongate member positioned coaxially with the first elongate member, wherein the second elongate member is coupled to a pump for performing an aspiration function on the clot. The robotically controlled system may also include an instrument drive system for driving the instrument system. The instrument drive system may include a first instrument driver for driving the first elongate member and a second instrument driver for driving the second elongate member.

In some embodiments, the robotically controlled system may further include a third elongate member that is positioned within the first elongate member and the second elongate member. The third elongate member may be capable of physically modifying the clot. The third elongate member may be a blade. The third elongate member may be a distal guard.

In one aspect, the robotically controlled system may further include a fourth elongate member positioned within the third elongate member. The fourth elongate member may be a guidewire.

In another aspect, the first elongate member may be an inflatable member for occluding a vessel. The first instrument driver may be coupled to first robotic arm and the second instrument driver may be coupled to a second robotic arm. The first robotic arm and the second robotic arm may be positioned on an adjustable arm support. The adjustable arm support may be positioned on one side of a patient platform and an opposing adjustable arm support may be positioned on an opposite side of the patient platform. The first robotic arm and the second robotic arm may be coupled to a movable cart.

In some embodiments, the robotically controlled system may further include a console for navigating the instrument through the patient. The console may include a controller in the form of a pendant, gimbal or joystick for driving the instrument through the patient.

In another aspect, the first elongate member may be capable of being articulated independently from the second elongate member. The first elongate member may include at least one articulation cable and the second elongate member may include at least one articulation cable. The first elongate member may include a greater number of articulation cables than the second elongate member.

In some embodiments, the robotically controlled system may include a processor system for assisting in task prioritization. The processor system may be capable of gathering information related to one or more of a location of an occlusion and/or a severity of blockage by the clot.

In one aspect, both the first elongate member and the second elongate member are robotically controlled. In some embodiments, only one of the first elongate member and the second elongate member is robotically controlled.

One aspect relates to a method of clot removal, the method includes: driving a robotically controlled instrument system toward a clot within vasculature of a patient, wherein the instrument system comprises a first elongate member and a second elongate member positioned coaxially with the first elongate member; and applying a pump of the second elongate member to aspirate the clot.

In some embodiments, the first elongate member is coupled to a first instrument driver and the second elongate member is coupled to a second instrument driver. The first instrument driver may be coupled to a first robotic arm and the second instrument driver may be coupled to a second robotic arm.

In one aspect, the method may further include comprising driving a third elongate member within the vasculature of the patient. The method may further include piercing the clot via the third elongate member. The method may further include deploying a distal guard along a length of the third elongate member that is downstream from the location of the cloth.

In another aspect, the first elongate member and the second elongate member may be driven in tandem. The first elongate member and the second elongate member may be driven independently from one another.

In some embodiments, the method may further include displaying a first view on a screen of a representation of the vasculature and a representation of the instrument system therein. The first view may be a first person view. The first view may be a third person view.

In one aspect, the method may further include displaying a second view on the screen of a representation of the vasculature and a representation of the instrument system therein, wherein the first view is different from the second view. The method may include switching between the first view and the second view.

The method may further include displaying an indicator on the first view, wherein the indicator indicates a concentricity of the instrument system within the vasculature of the patient. The method may further include generating a 3-D image based on pre-operational images.

The method may further include identifying a clot on the 3-D image. The method may further include identifying a pathway on the 3-D image that represents a path between the instrument system and the clot.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
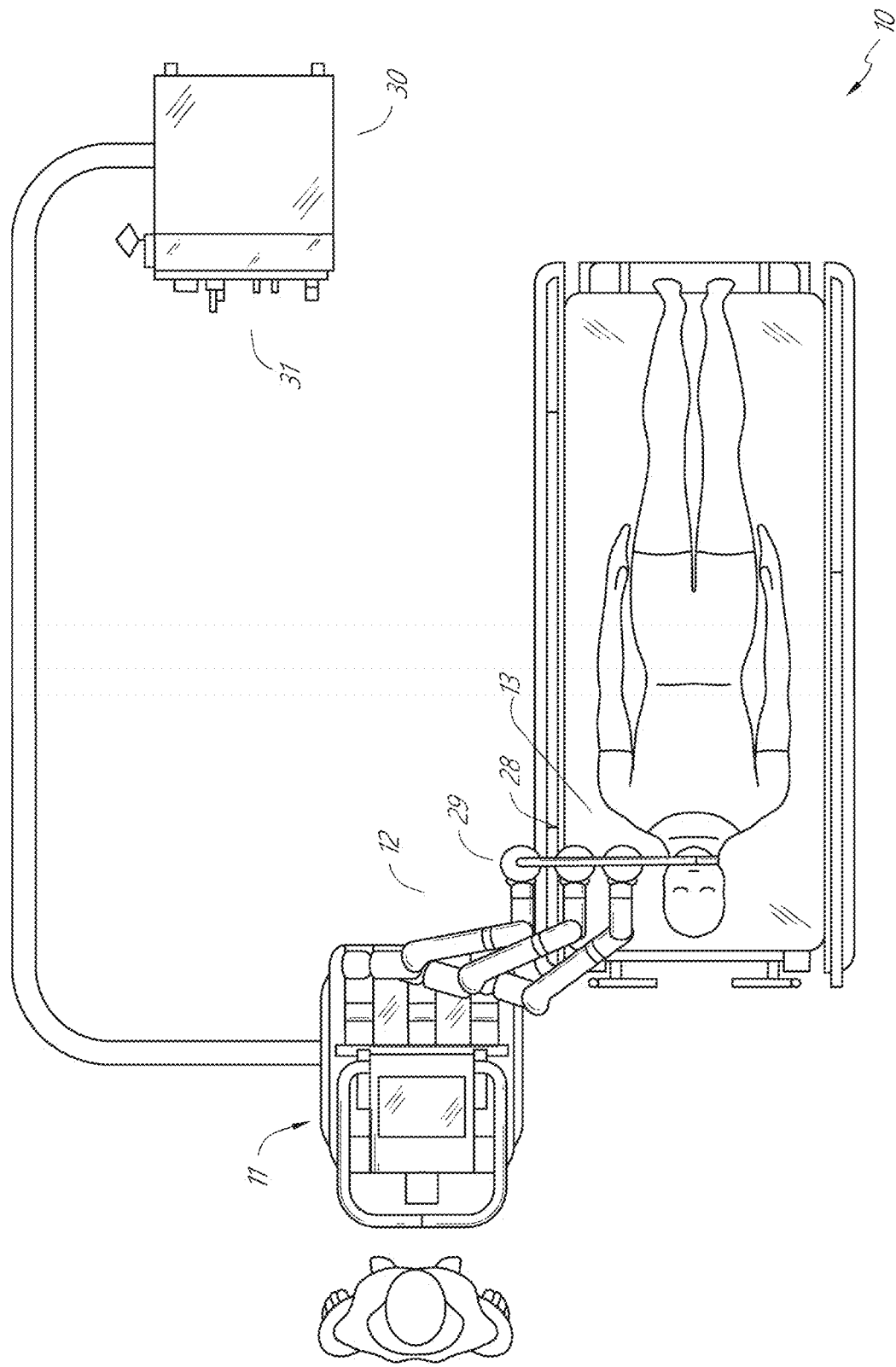
FIG. 1 illustrates an embodiment of a cart-based robotic system arranged for diagnostic and/or therapeutic bronchoscopy procedure(s).
Figure 2:
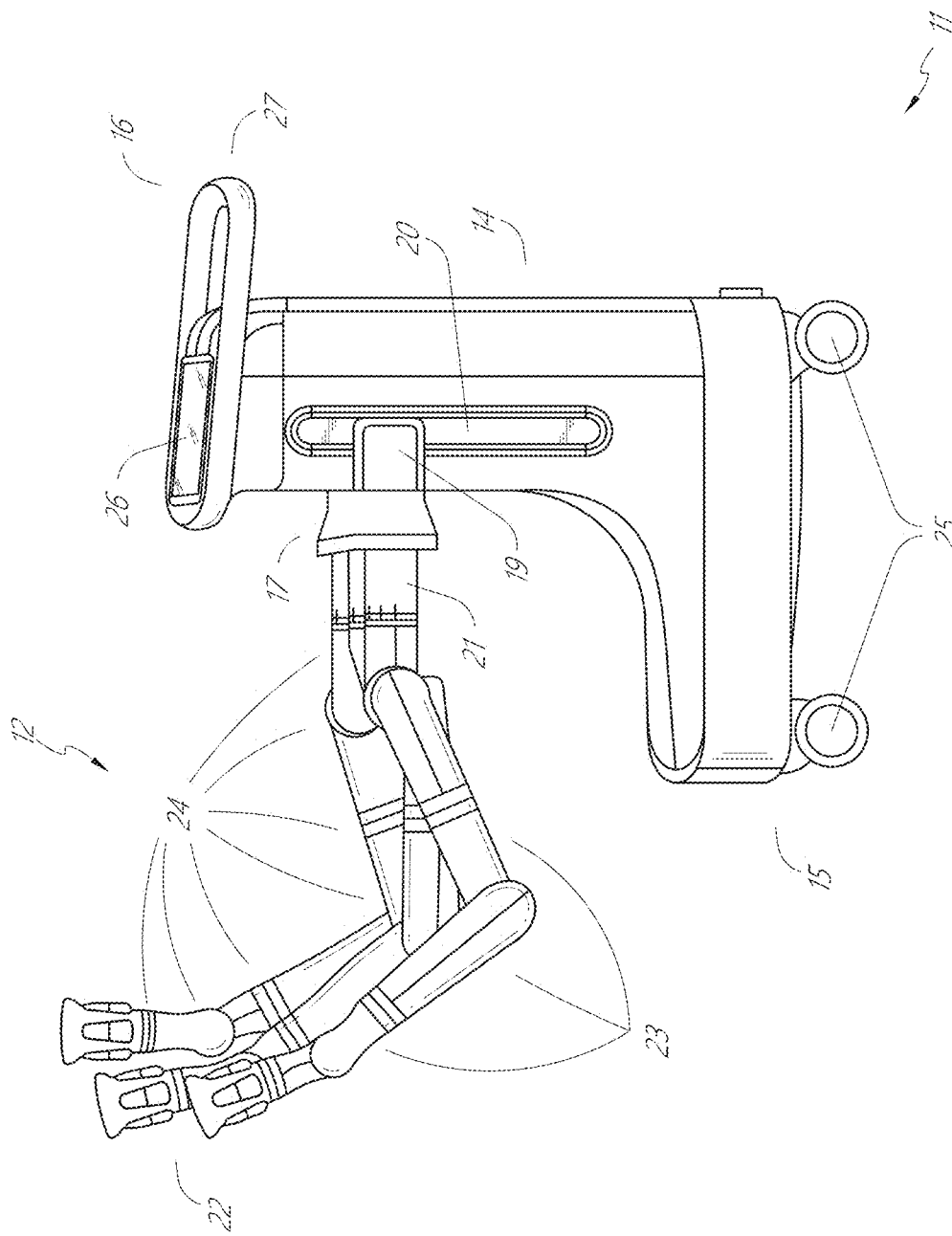
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
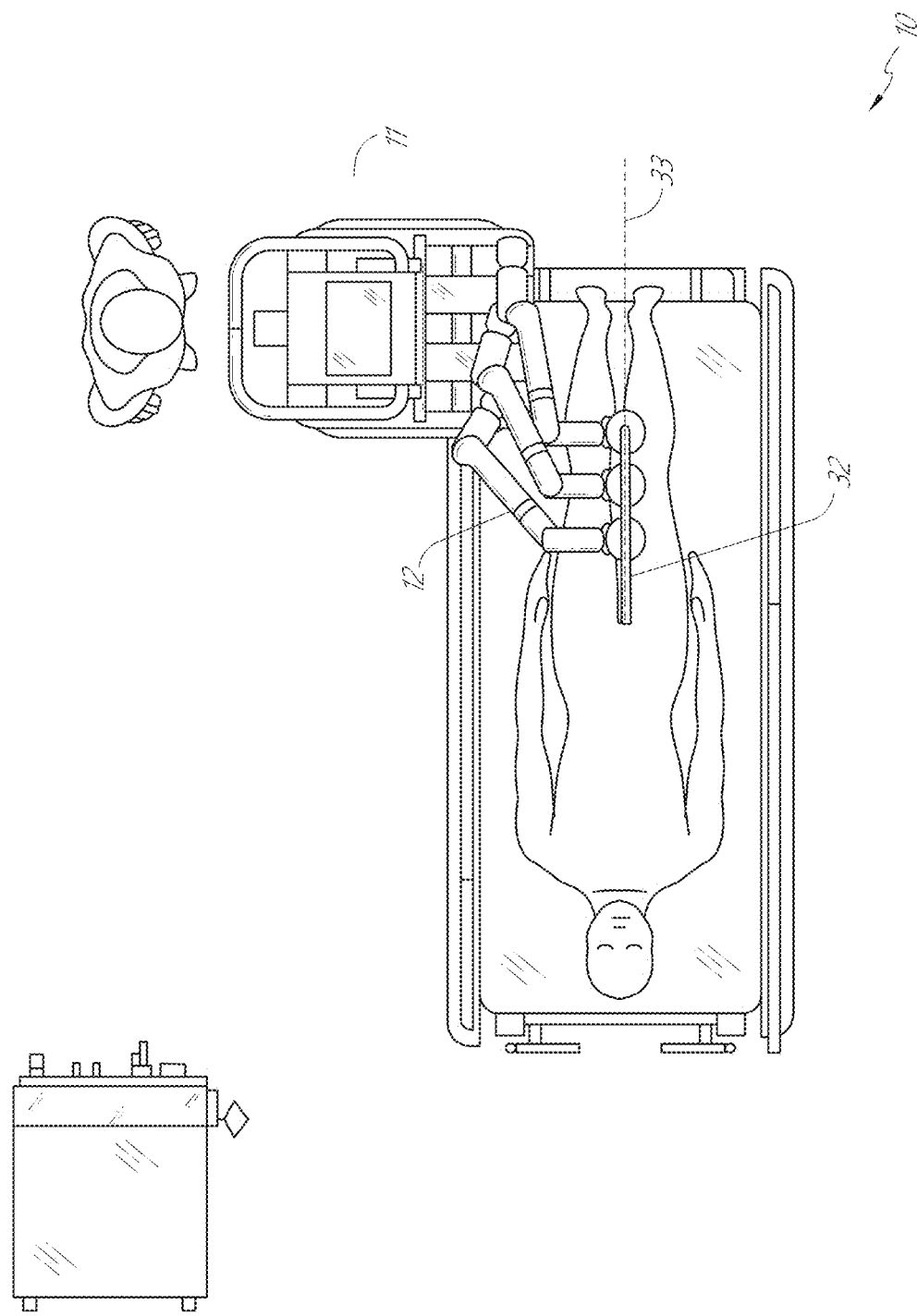
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
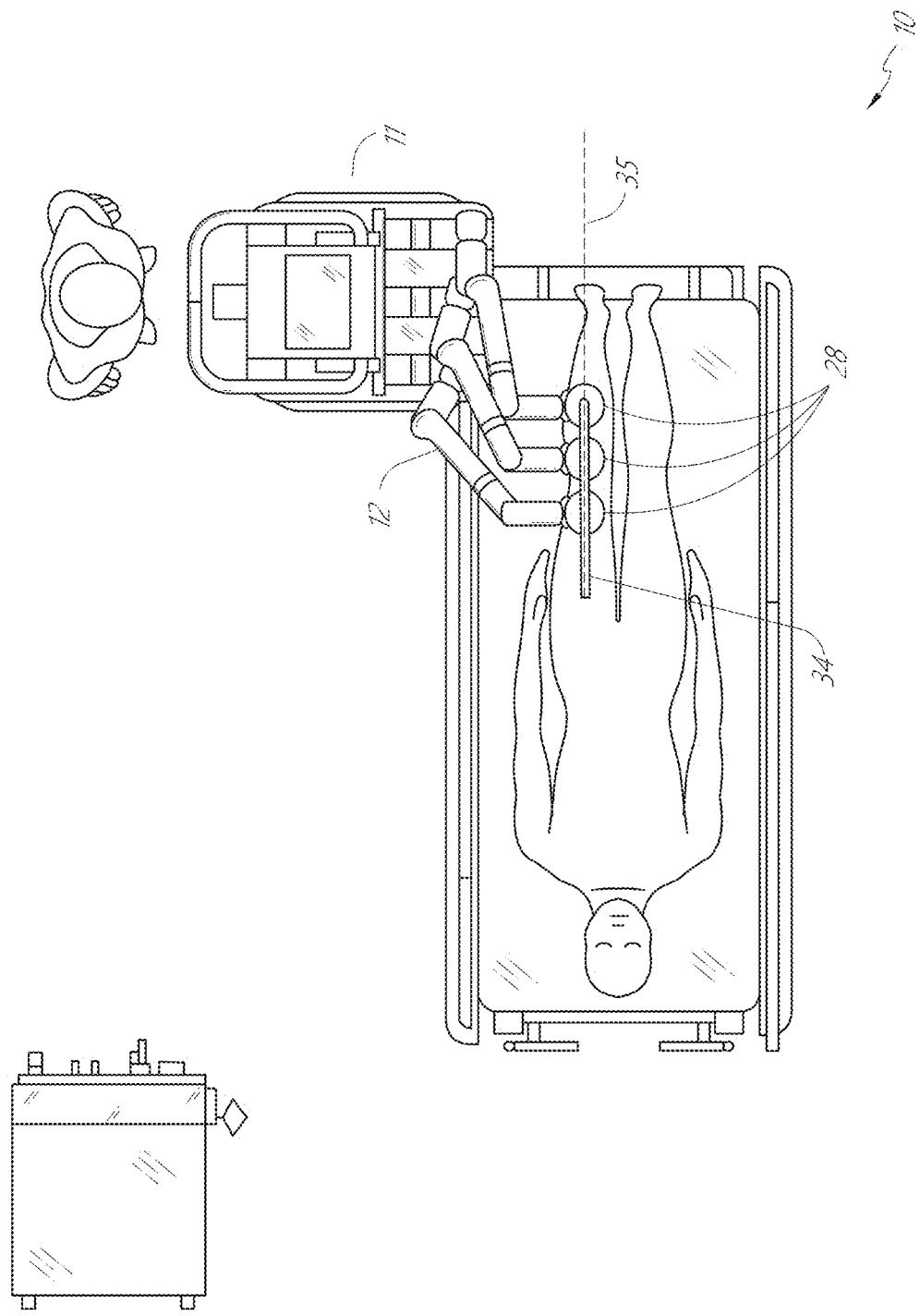
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
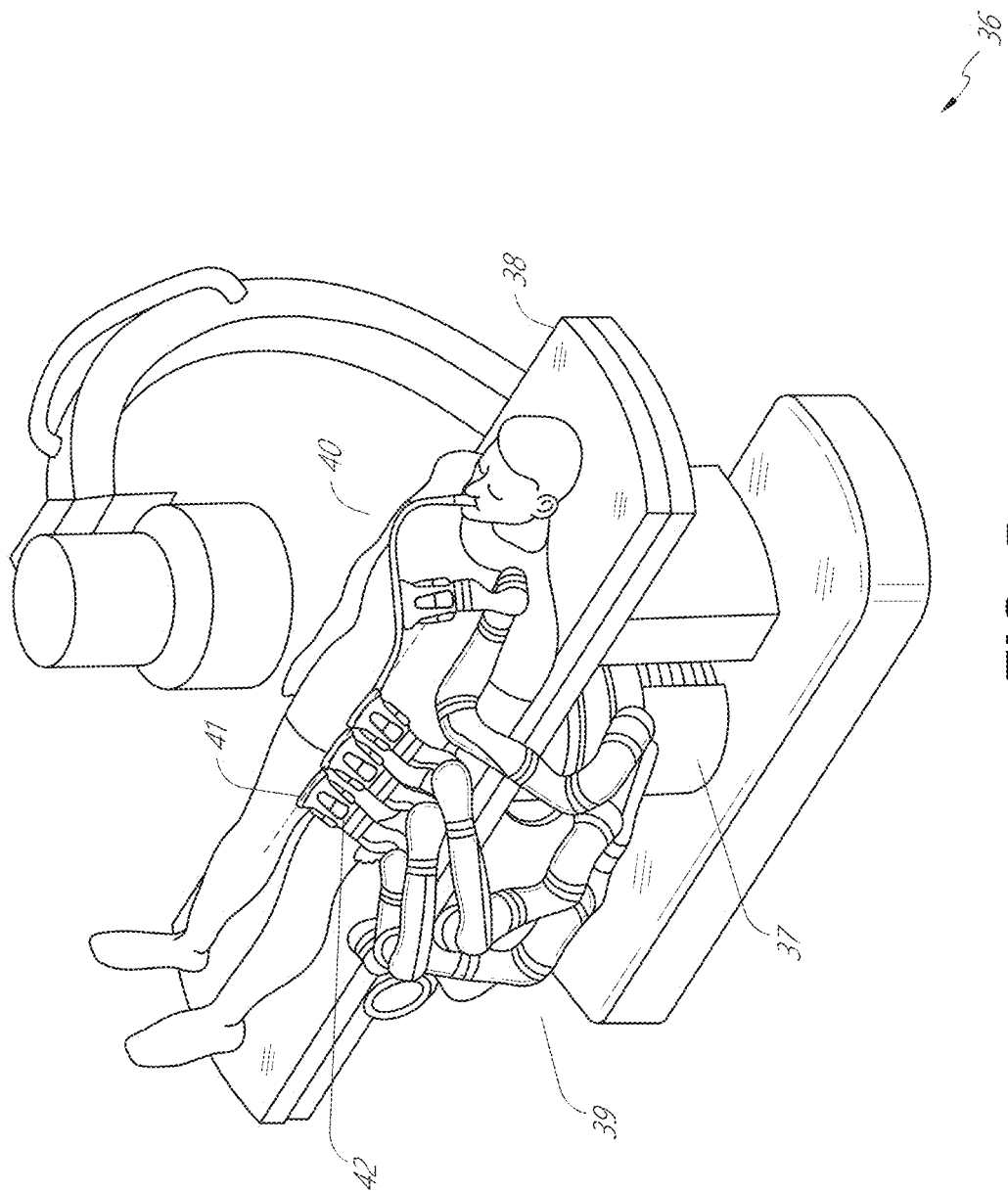
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
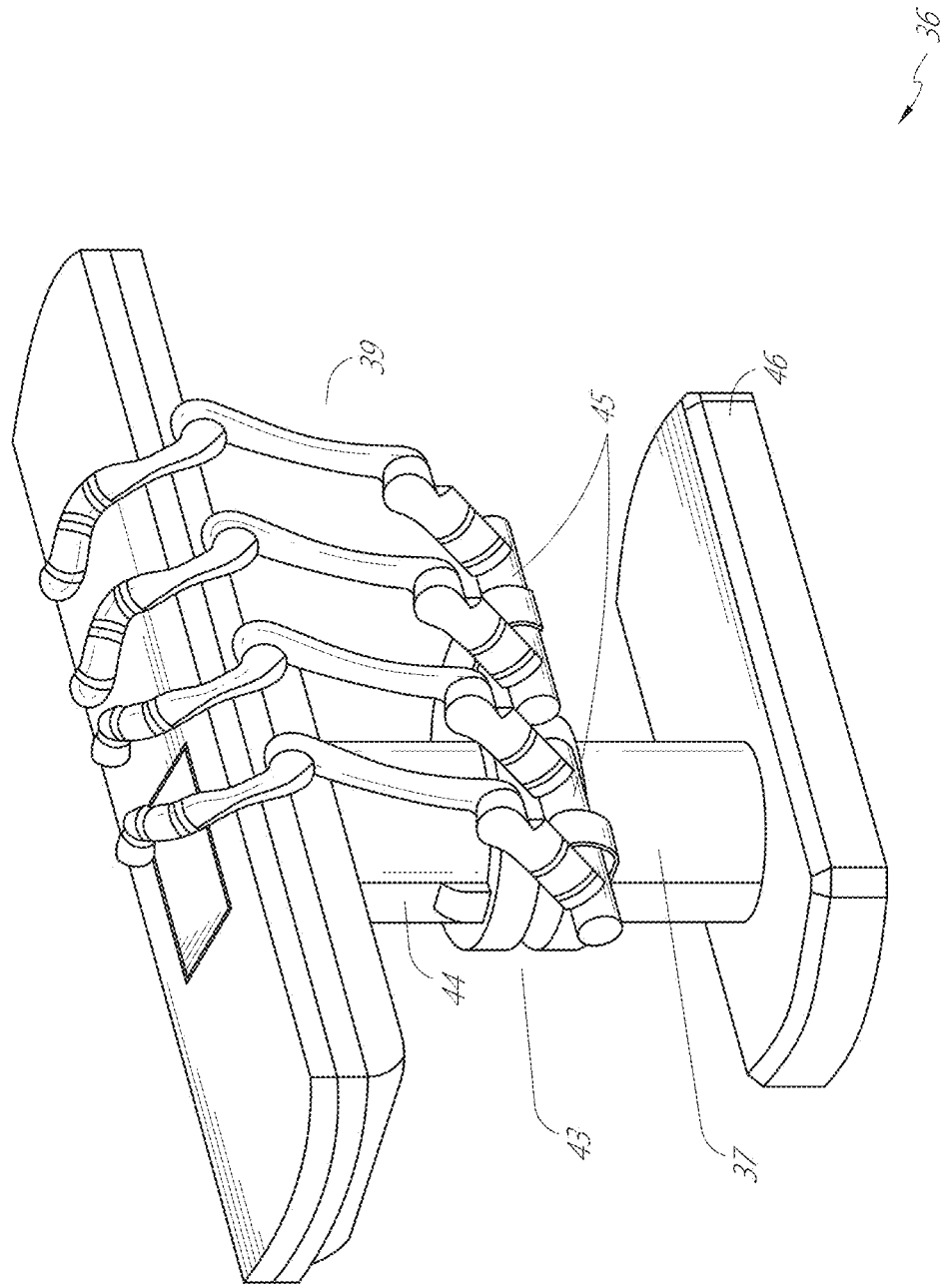
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
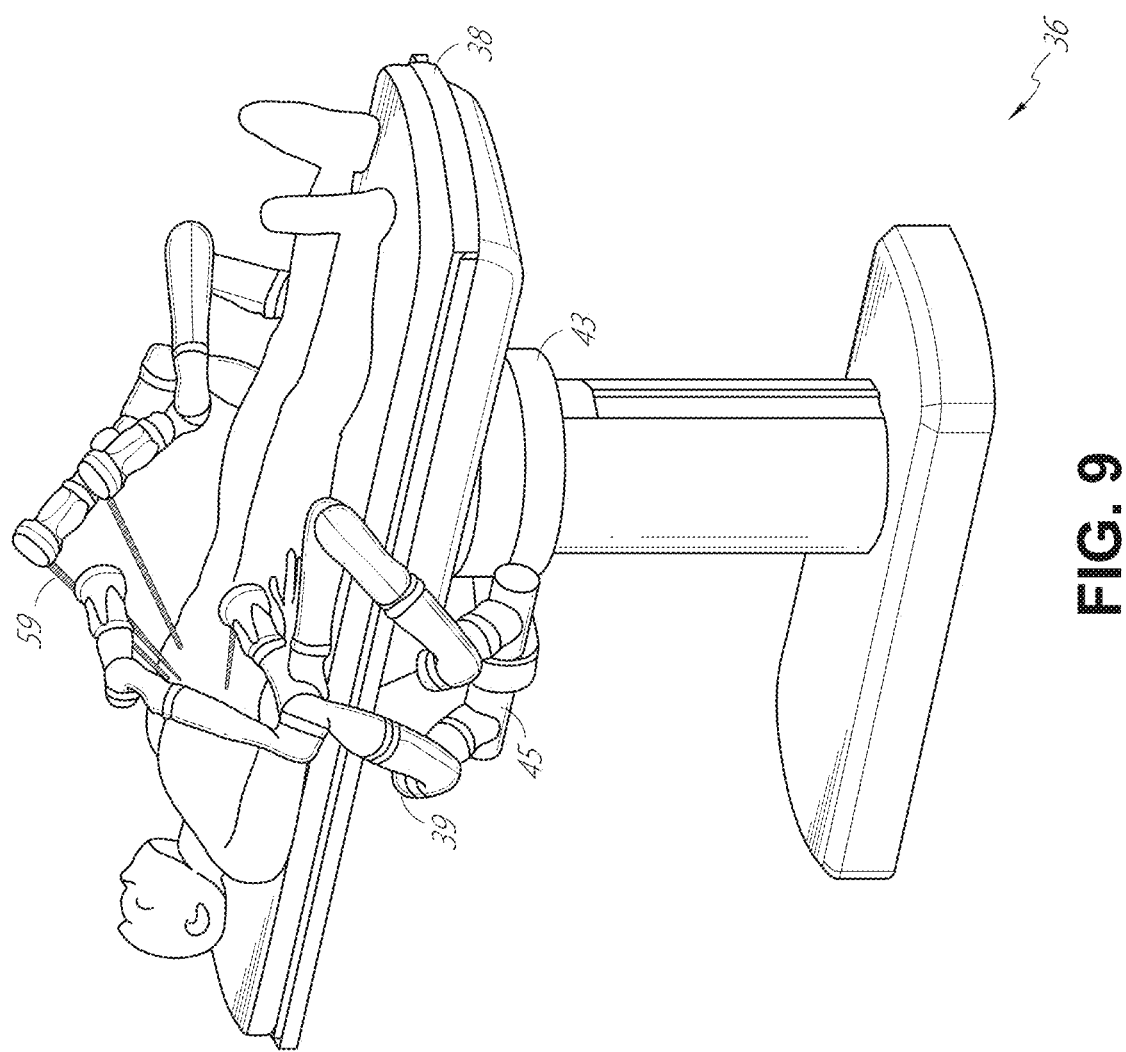
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
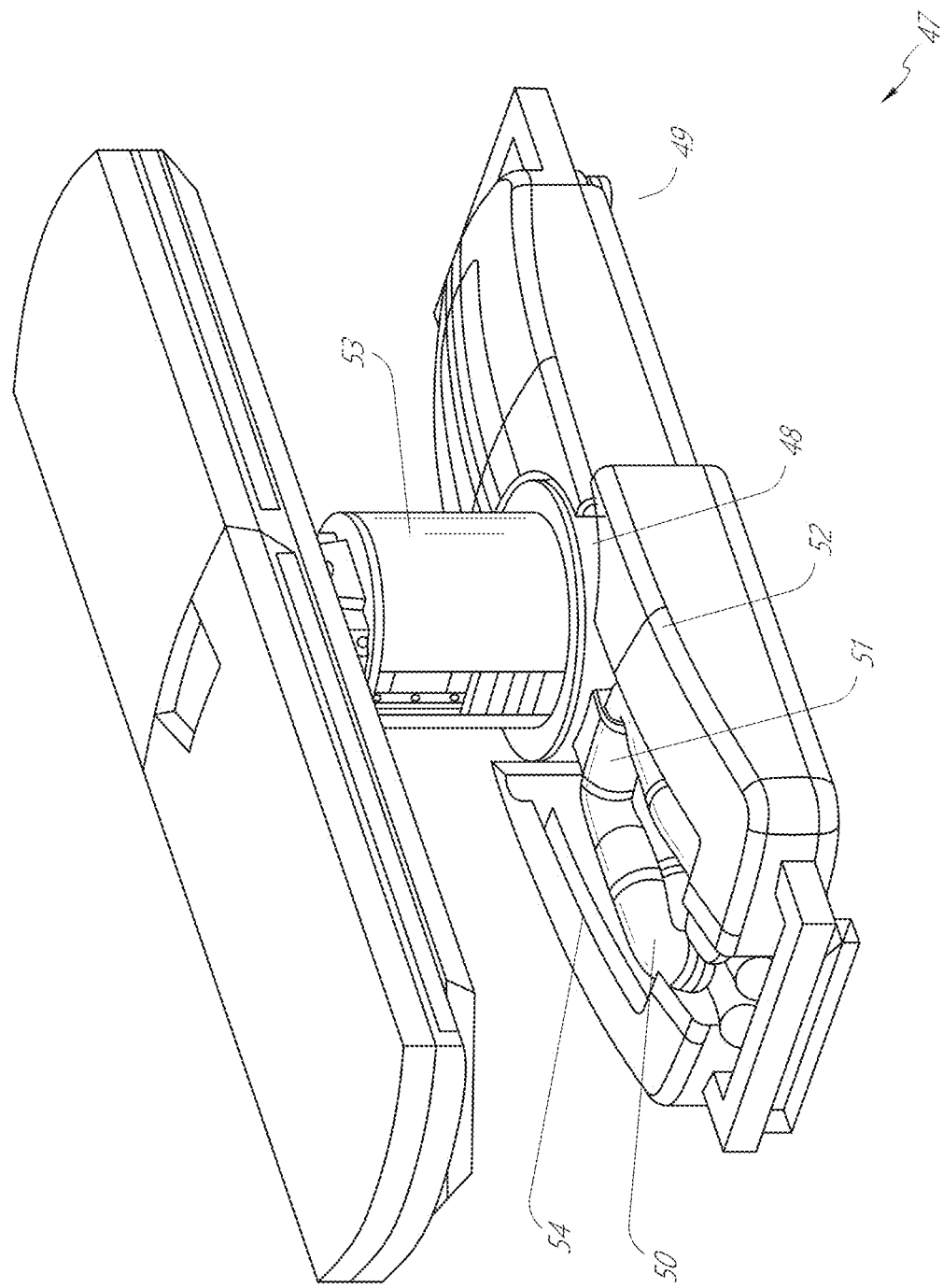
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
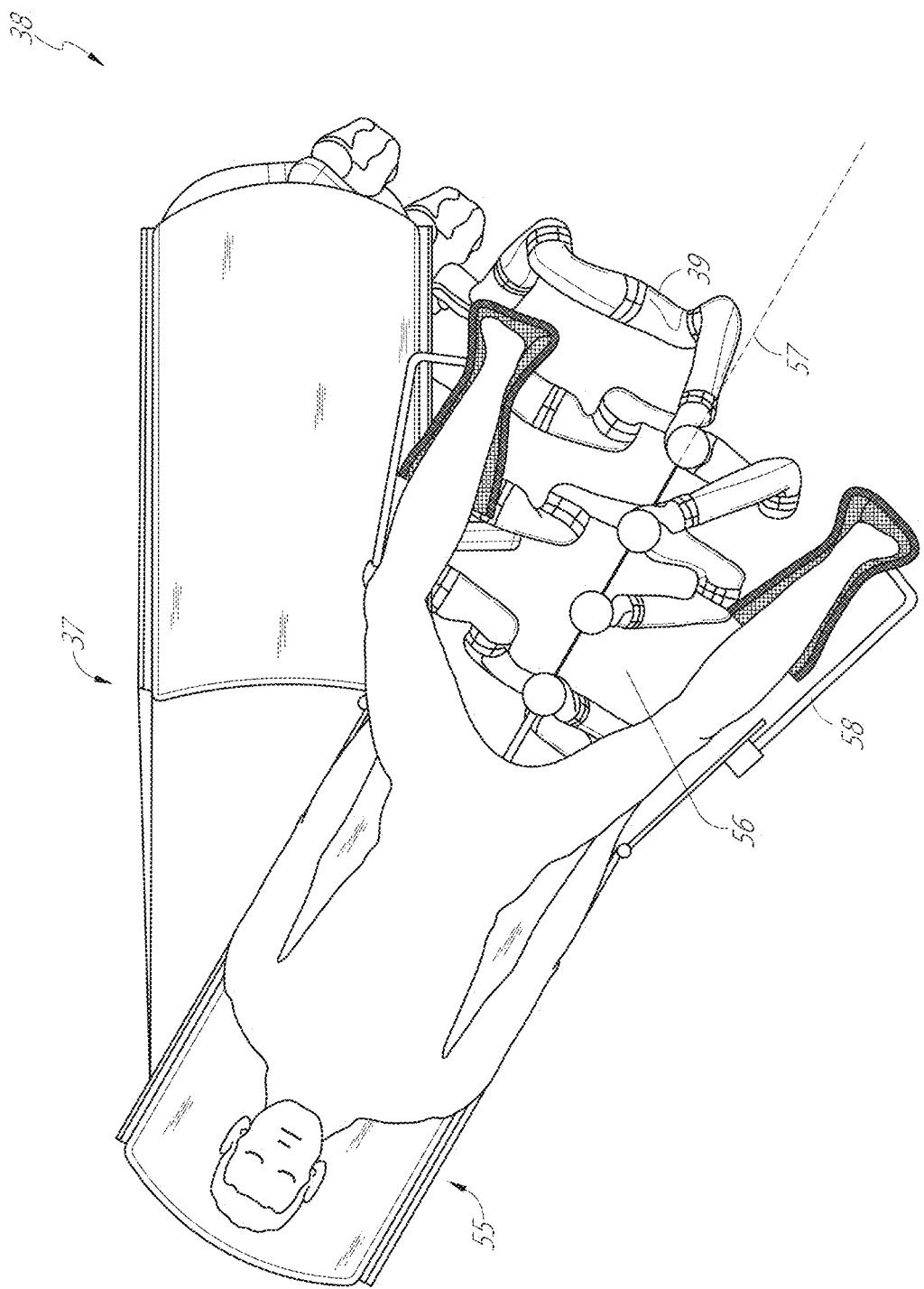
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
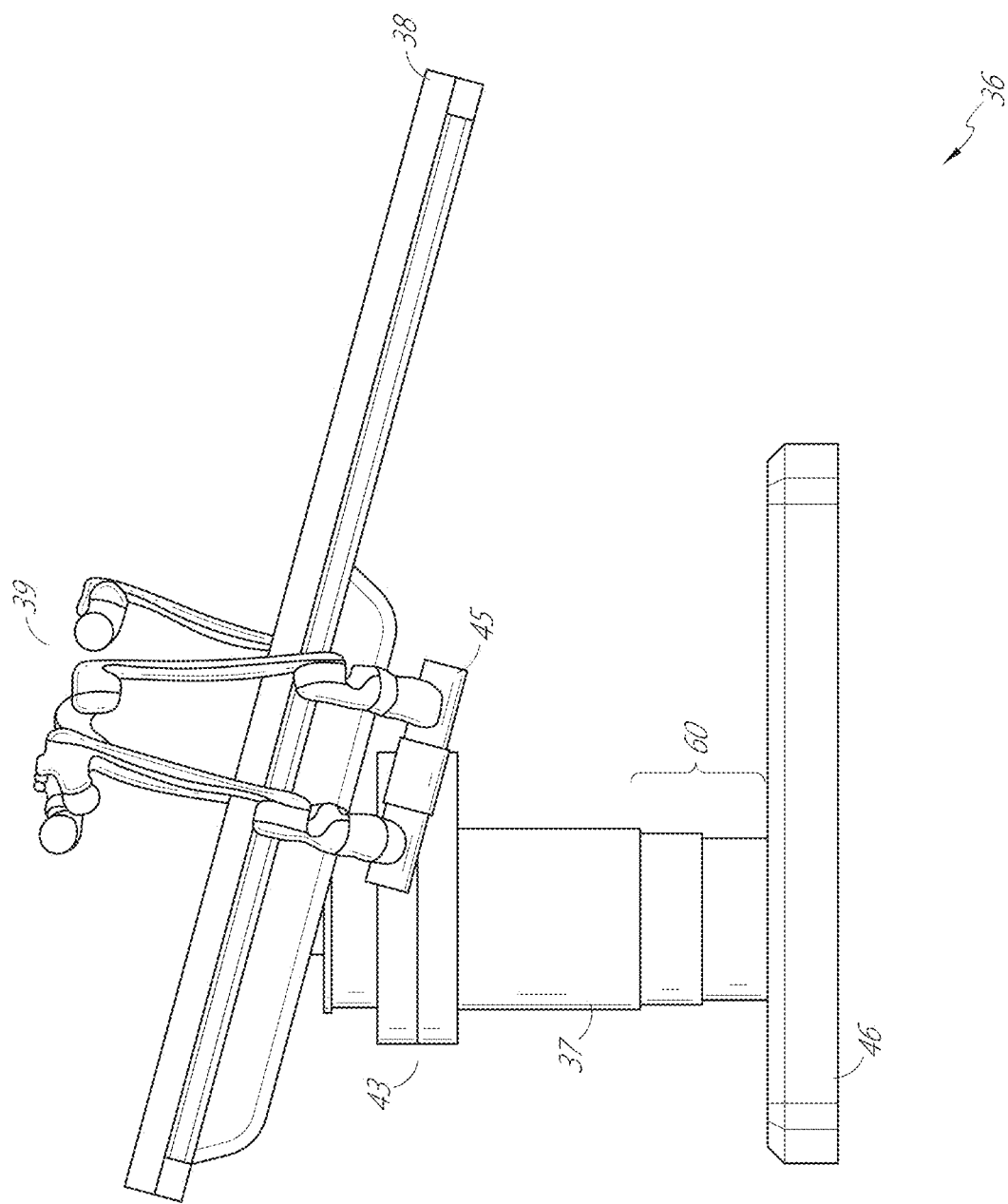
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
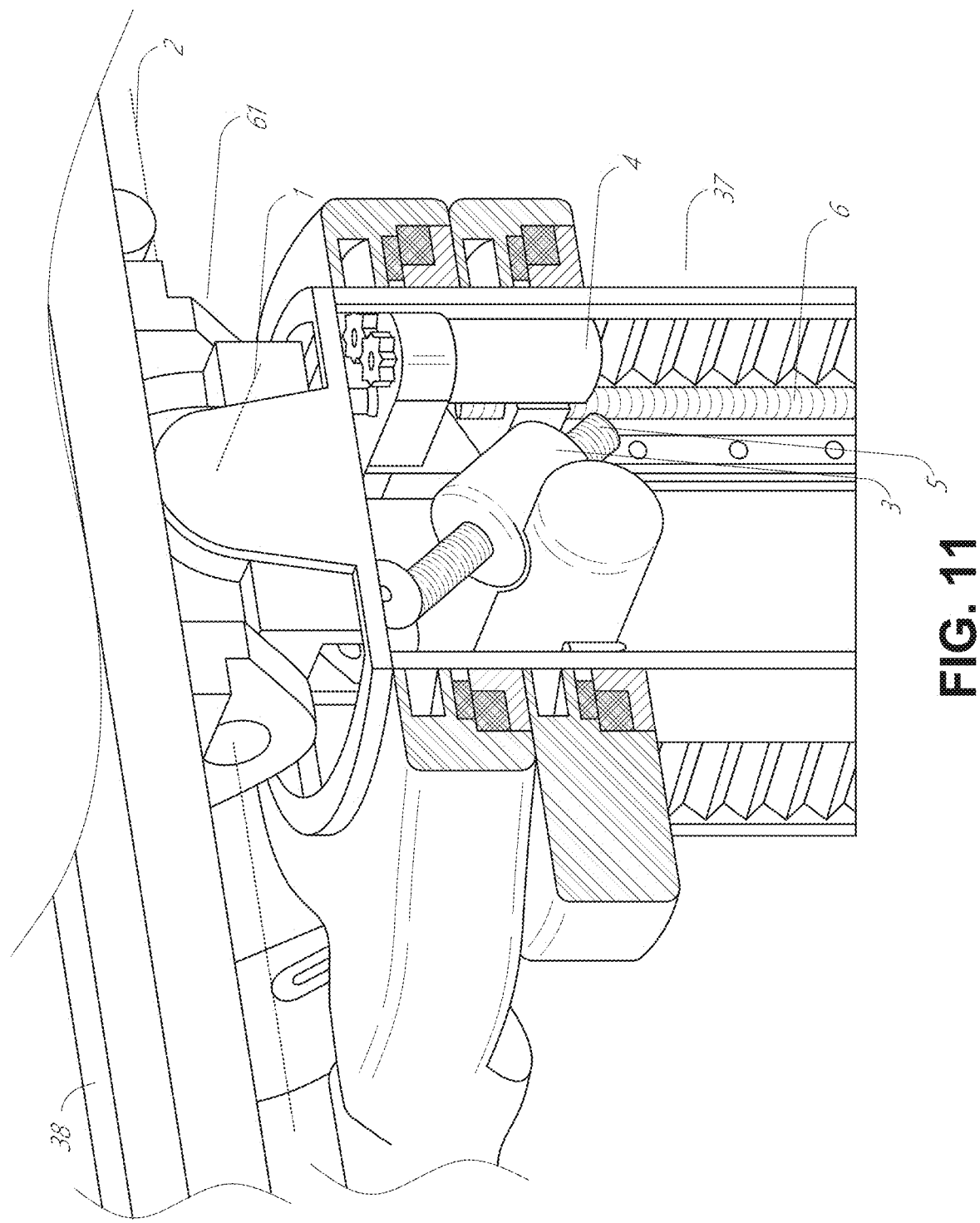
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
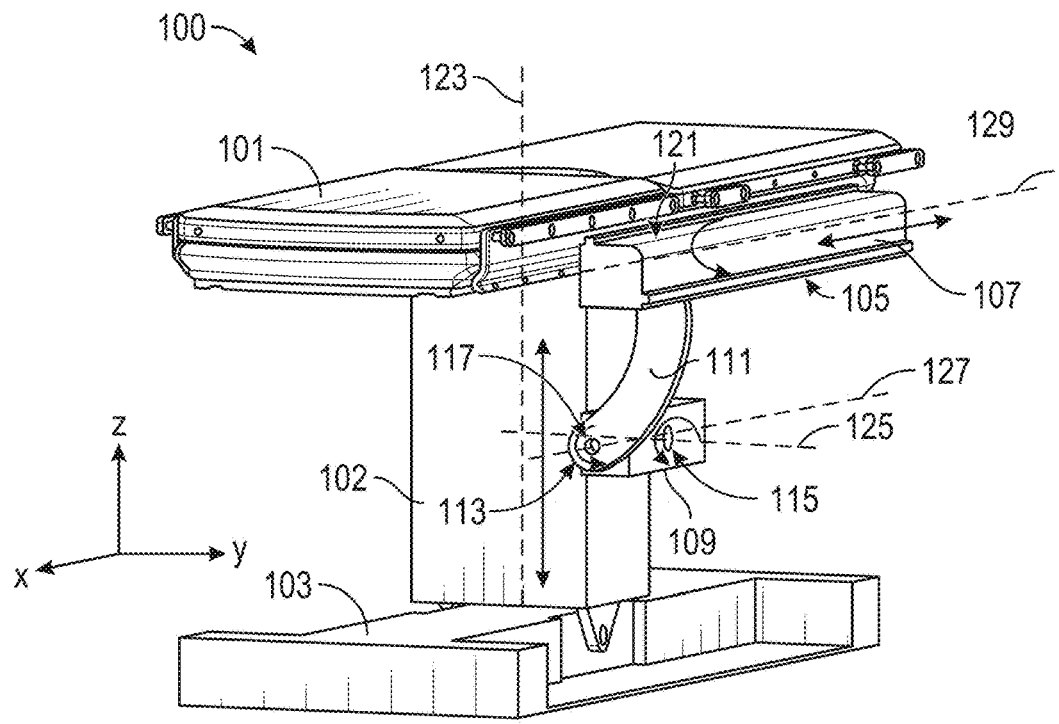
FIG. 12 illustrates an alternative embodiment of a table-based robotic system.
Figure 13:
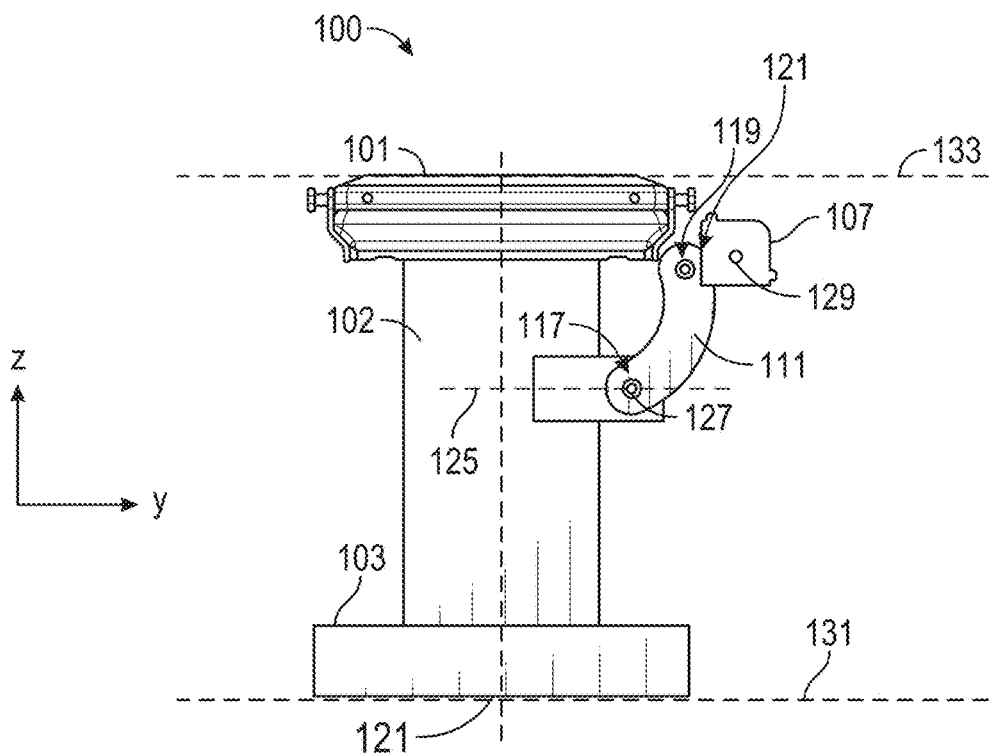
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
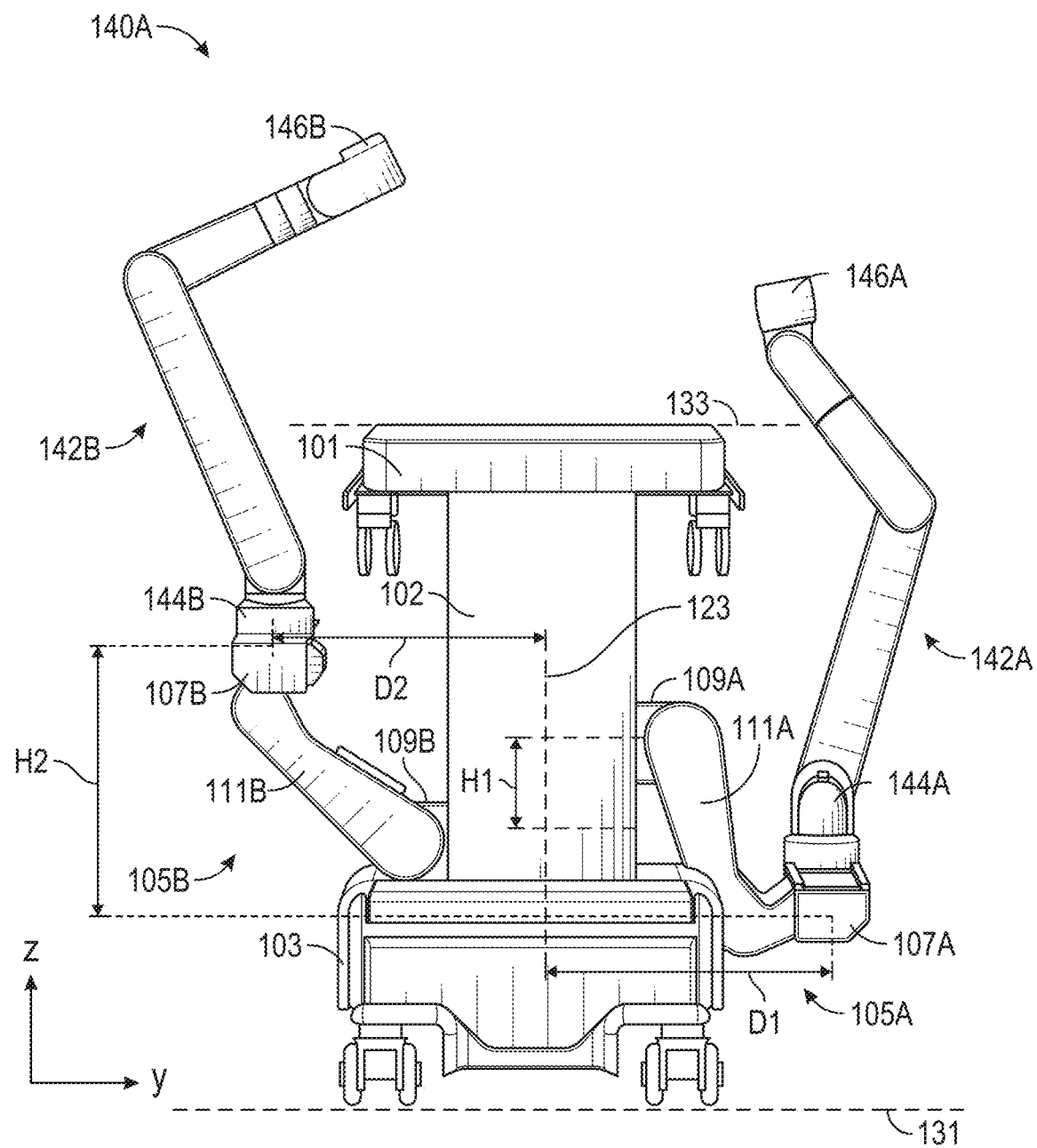
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
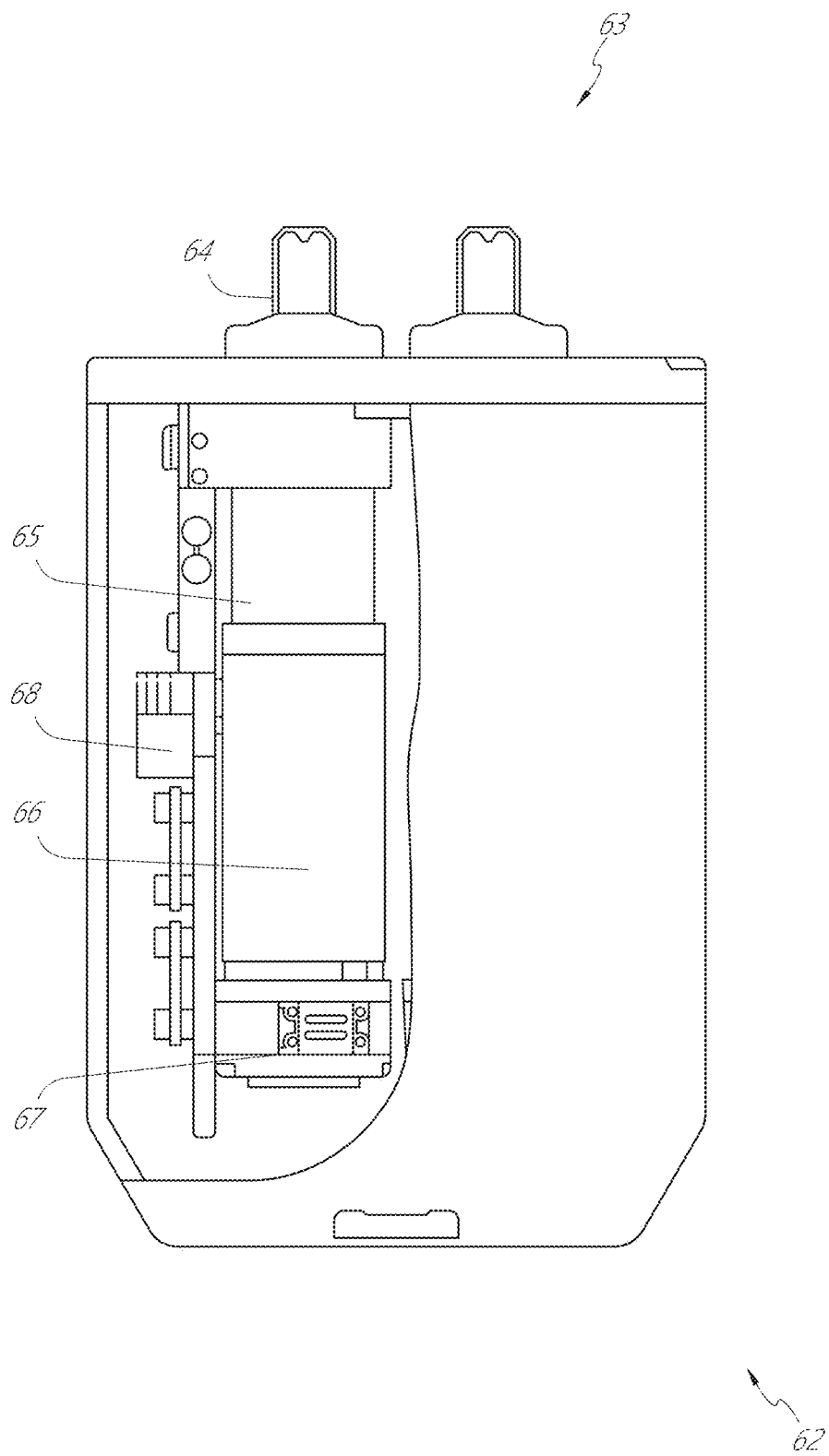
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
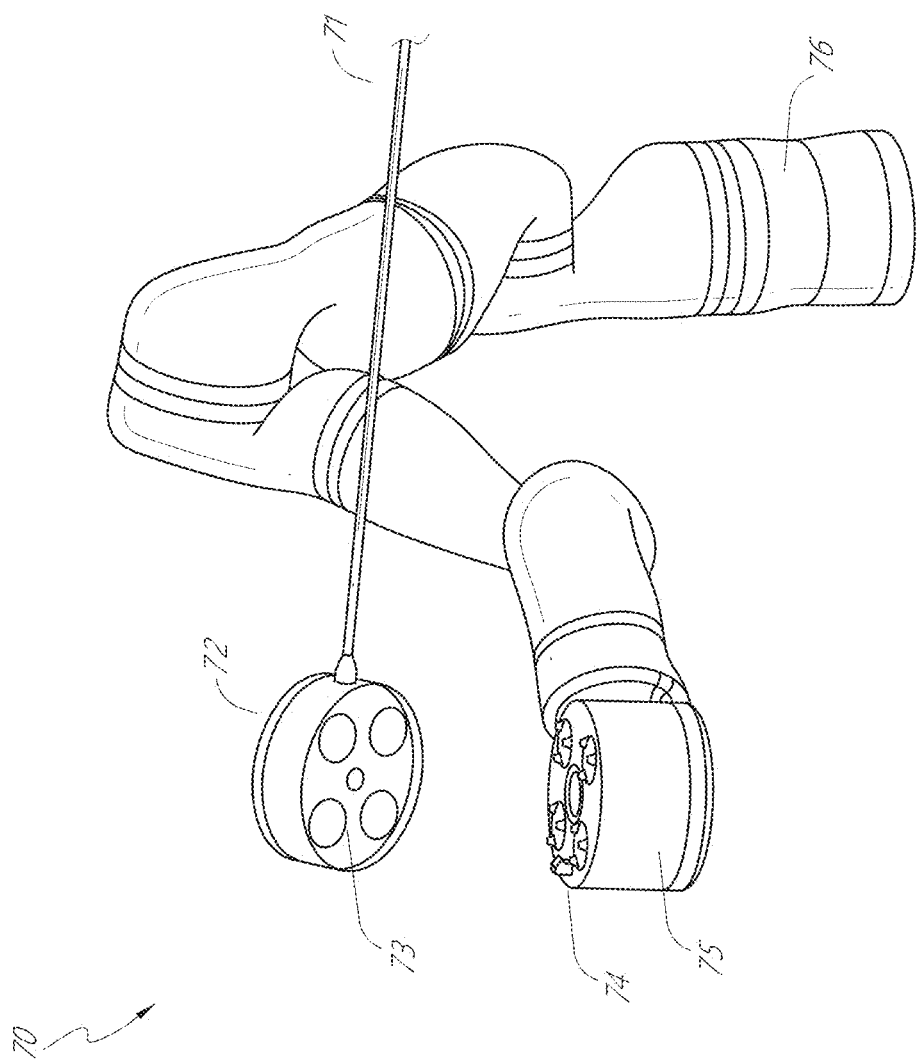
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
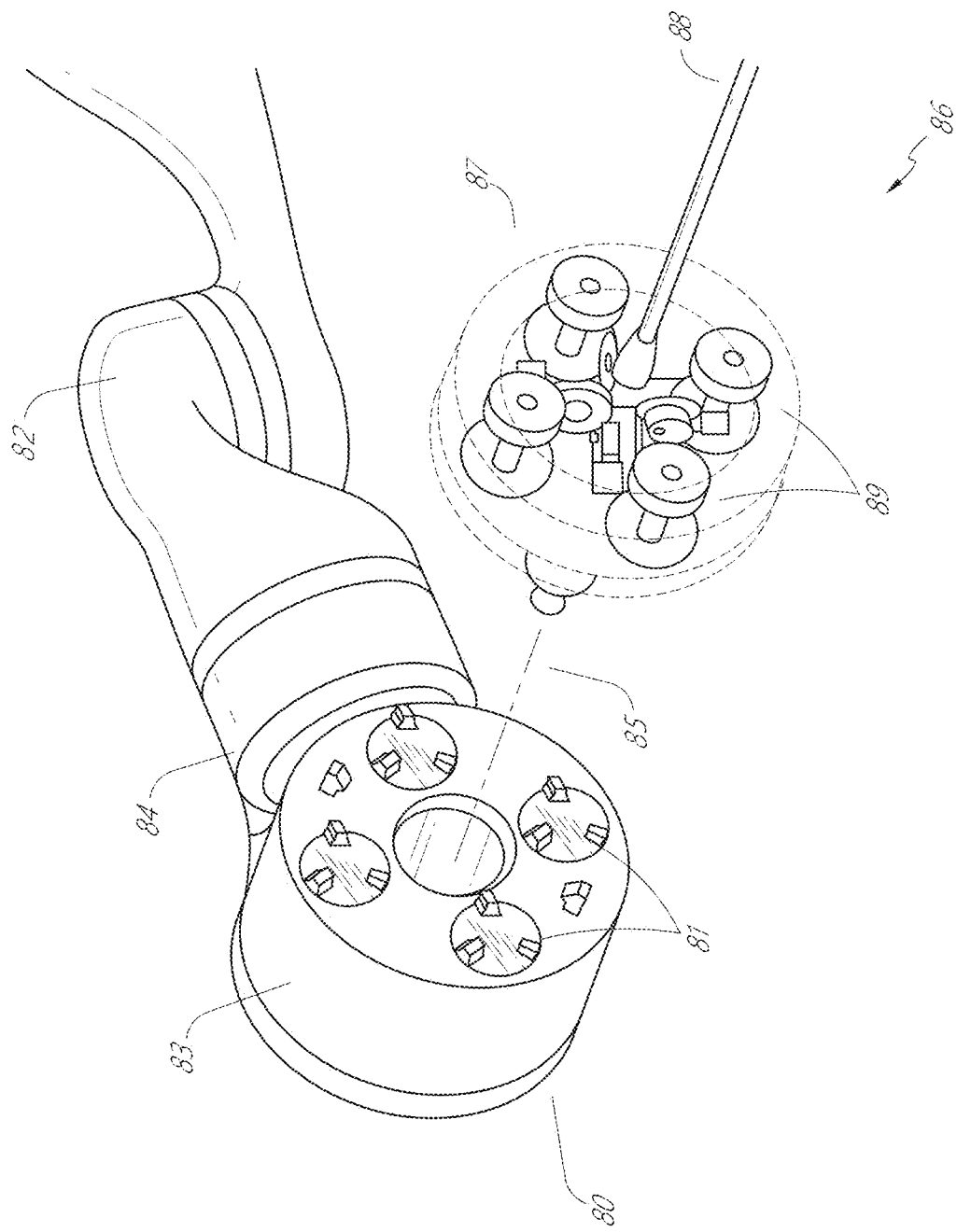
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
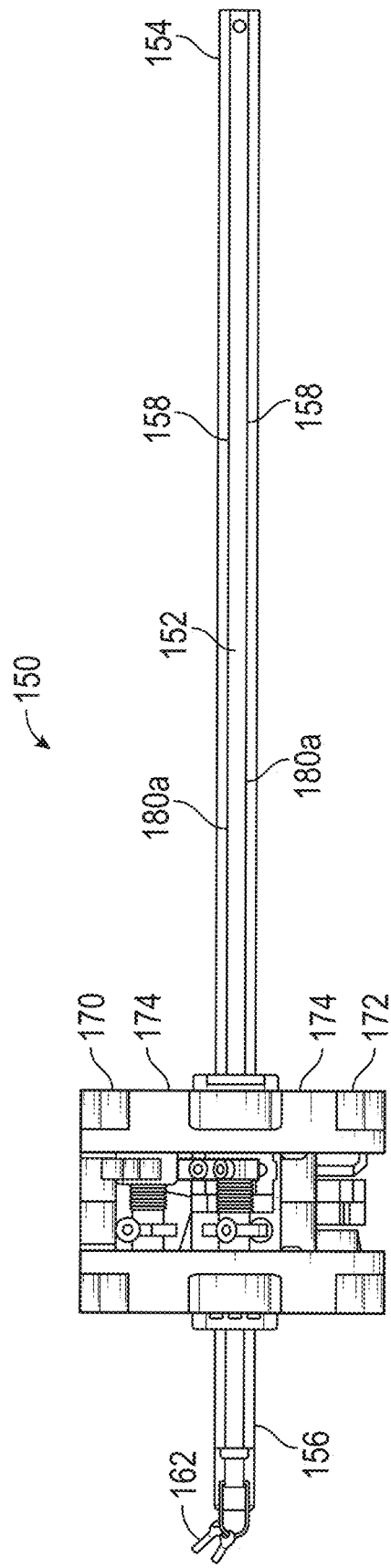
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
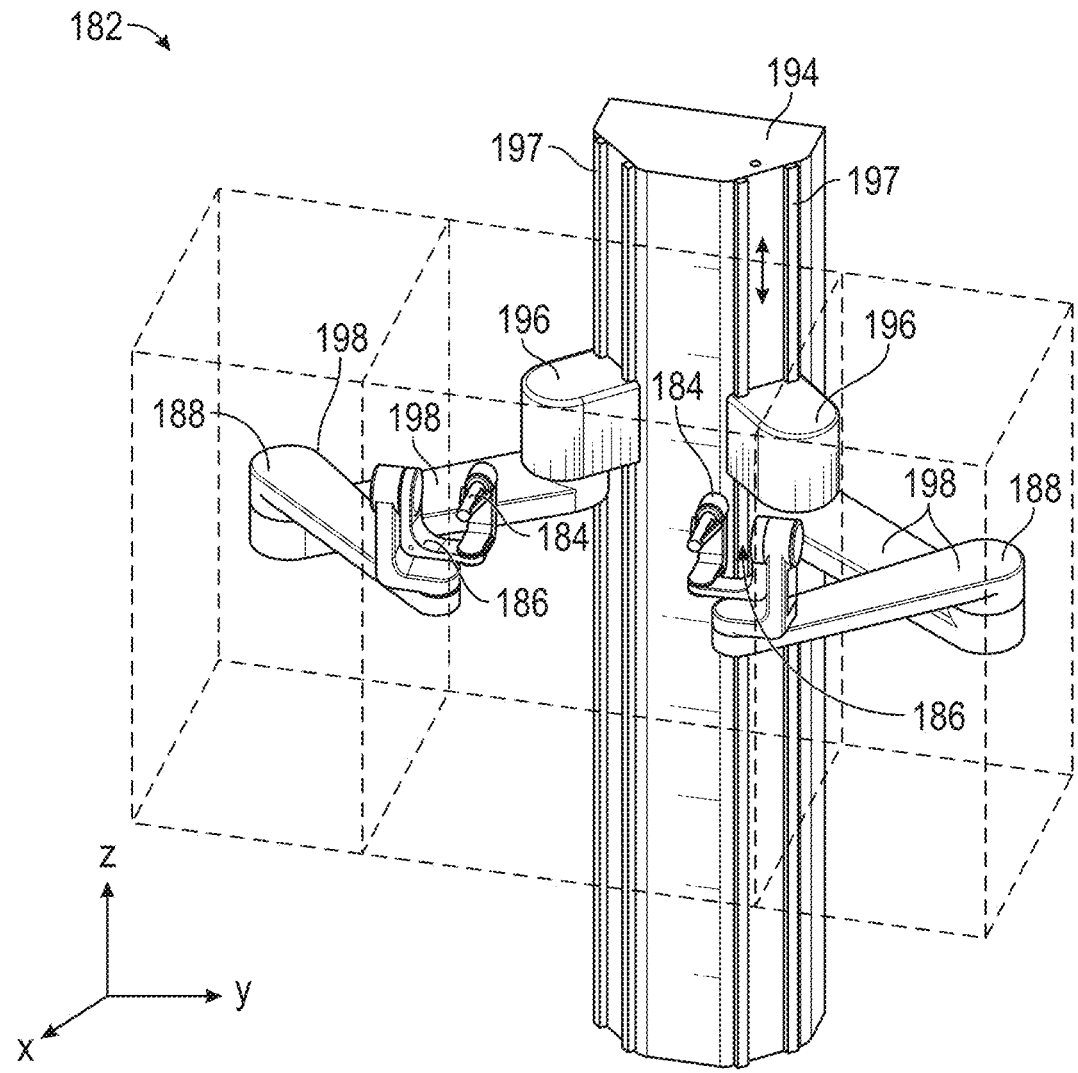
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
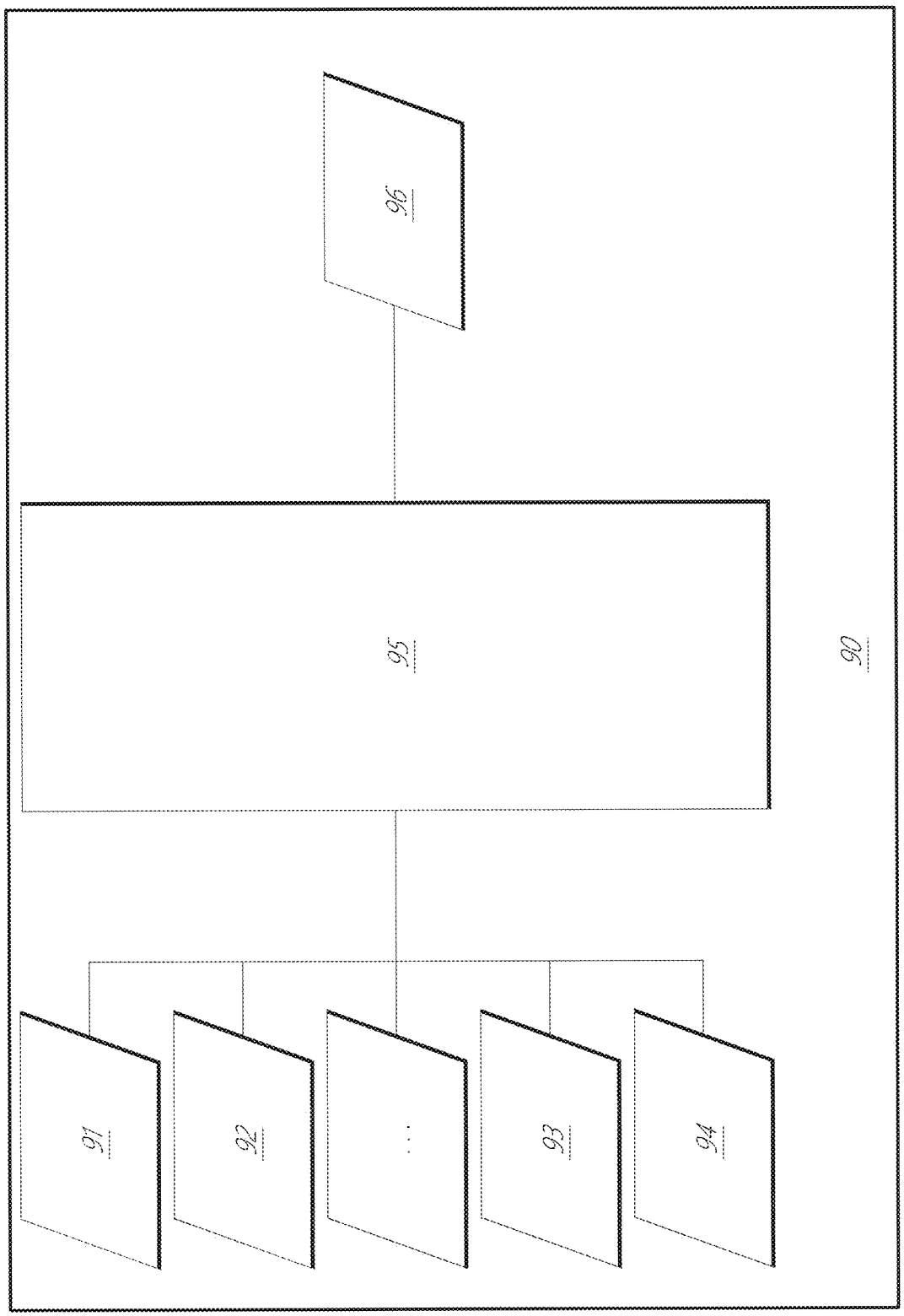
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Robotically Controlled Clot Manipulation and Removal.

Embodiments of the disclosure relate to systems and methods for robotically controlled clot manipulation and removal. Acute ischemic strokes present a major health issue facing the general populace. These strokes can be caused by large vessel occlusions due to clots formed in blood vessels.

Current procedures for clot removal are performed manually by a vascular/neurovascular surgeon that has to navigate a tortuous path to access cerebrovasculature. These manual procedures can face a number of challenges, including incomplete clot removal (25% of cases), multiple catheter passes (50% of cases), emboli disruption, and vessel dissection/perforation. In addition, the time for performing such a procedure can be quite long, with the result being rapid loss of neurons as each minute passes. Furthermore, in addition to a vascular surgeon, multiple other personnel may be needed to complete a stroke procedure, including neurologists, radiologists, nurses and catheter lab clinicians, thereby consuming a large number of resources. Often times, physicians who are capable of performing stroke care are often in limited supply or not readily available at a time of need for a patient seeking treatment.

Embodiments described herein cover systems and methods for robotically controlled manipulation and removal of clots that address issues described above. The systems are configured such that at least a portion of the clot removal procedure can be performed robotically, thereby making clot removal more accurate and faster to perform. While the systems and methods described herein often refer to clots in the cerebrovasculature, one skilled in the art will appreciate that the systems and methods described can also apply to clots found anywhere in the body, including in the peripheral and pulmonary arteries.

A. Robotic Systems for Performing Clot Removal.

Robotic systems for performing clot removal will now be described. These systems can be used to control at least some portion of a clot removal instrument robotically. As shown in FIGS. 26-29C, clot removal instruments can take many forms, and can include multiple elongate members, including one or more sheaths, catheters, disruptors and guidewires. In some embodiments, the robotic systems can be used to navigate, steer and/or articulate one or more of these sheaths, catheters, disruptors and guidewires robotically via telemanipulation.

Figure 21:
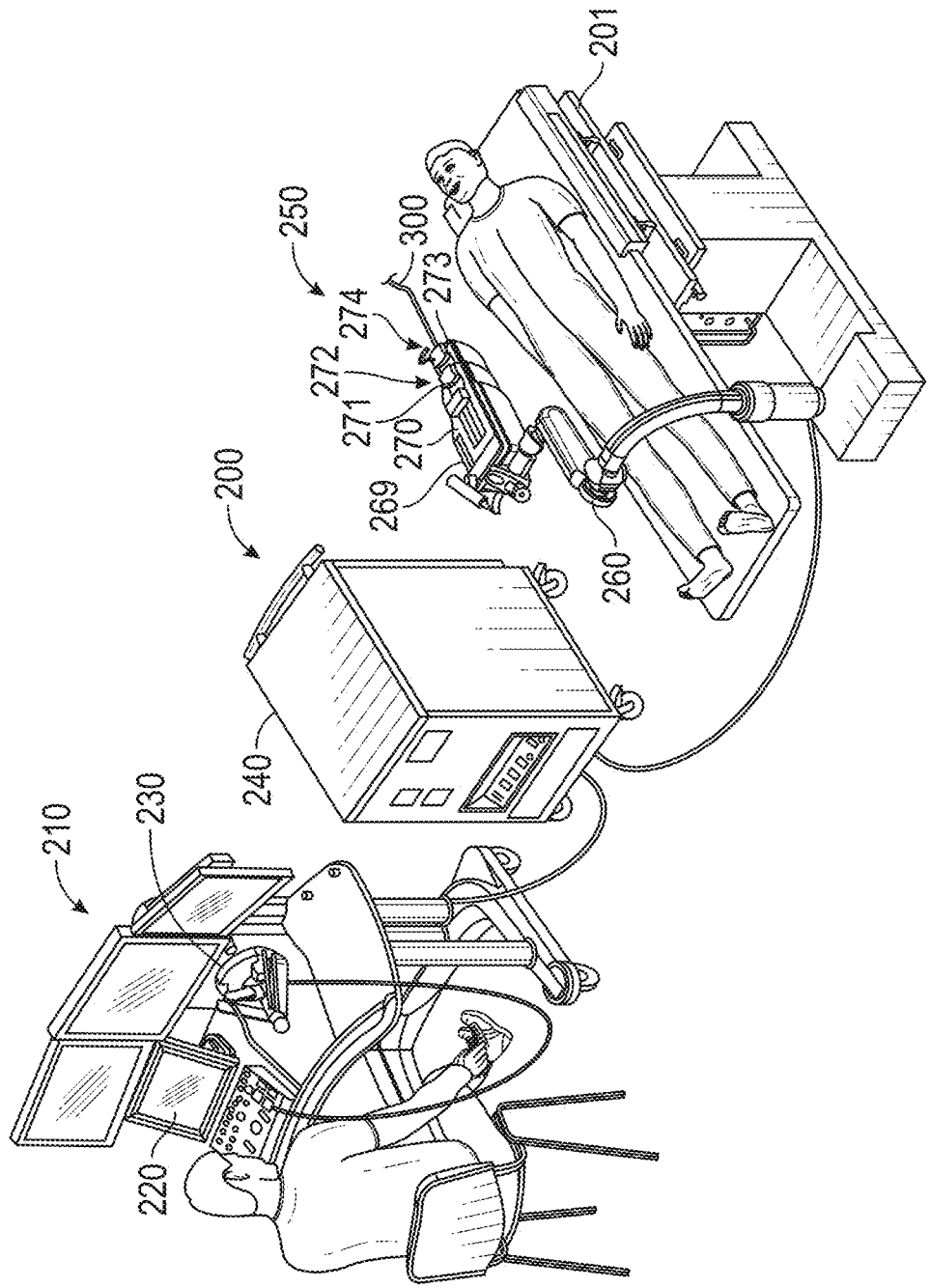
FIG. 21 illustrates an embodiment of a robotic system for performing clot removal.

FIG. 21 illustrates an embodiment of a robotic system 200 for performing clot removal. The robotic system 200 comprises a console 220, a processor 240, a patient platform 201 and an instrument drive system 250. The instrument drive system 250 is configured to manipulate a clot removal instrument 300 through a patient to remove a clot e.g., in cerebrovasculature, in peripheral vasculature or in a pulmonary vessel. While the application refers to reference numeral 300 as a clot removal instrument composed of multiple components (e.g., elongate members), one skilled in the art can appreciate that reference numeral 300 can also be viewed alternatively as a clot removal system comprised of a number of elongate instruments therein.

As shown in FIG. 21, a patient is configured to reside on a patient platform 201. The patient platform 201 can be in the form of a bed that is capable of tilting in multiple degrees of freedom. For example, in some embodiments, the bed is capable of Trendelenburg tilt and/or lateral tilt. The patient platform 201 is capable of support an instrument drive system 250. In some embodiments, the patient platform 201 is capable of support a pair of instrument drive systems 250.

The instrument drive system 250 comprises a set-up arm including a set-up joint 260 and an instrument driver 270. The instrument driver 270 comprises a base 269 that supports a proximal instrument driver 271 and a distal instrument driver 273 for driving instruments attached thereto via drive shafts (similar to the driver shown in FIG. 15). The proximal instrument driver 271 is connected to a proximal instrument splayer or handle 272 of the clot removal instrument 300, while the distal instrument driver 273 is connected to a distal instrument splayer or handle 274 of the clot removal instrument 300. In some embodiments, the proximal instrument driver 271 and distal instrument driver 273 are capable of aligning and/or translating relative to each other, such as along a track or rail. In other embodiments, the proximal instrument driver 271 and distal instrument driver 273 are capable of aligning and/or translating relative to each other via a virtual track via algorithm.

The clot removal instrument 300 comprises one or more elongate members capable of robotic control. In some embodiments, the one or more elongate members can be used for any of the following functions, including access, navigation, irrigation, suction, clot modification, and/or removal. In some embodiments, the clot removal instrument 300 can comprise a telescoping sheath or catheter that can serve as a conduit for a clot modifying or removal device that can remove a clot via any combination of aspiration, stent deployment, energy delivery, or drug delivery. In some embodiments, the clot removal instrument 300 can comprise at least one elongate member coupled to a proximal instrument handle 272 and at least one elongate member coupled to a distal instrument handle 274. As noted above, the proximal instrument handle 272 is connected to a proximal instrument driver 271, while the distal instrument handle 274 is connected to a distal instrument driver 273, thereby enabling driving and articulation of the respective elongate members.

The clot removal instrument 300 can be remotely and/or teleoperatively operated via a physician or clinician. The physician can be positioned at a console station 220 that includes one or more viewing screens 210 and a controller 230. The controller 230 can be used to drive, manipulate, and articulate the clot removal instrument 300. In some embodiments, the controller 230 can be in the form of a joystick, a pendant, or a gimbal. Advantageously, the viewing screens 210 can present one or more views to the user to assist in the navigation of the clot removal instrument 300, including but not limited to first-person, third-person, picture-in-picture, zoomed-out, and isometric views of the clot removal instrument 300 within a vessel. In addition, the viewing screens 210 can be touch screens whereby the user can interact with the screens to switch between images, modify image quality, and perform any other function to assist in imaging and navigation. As the physician manipulates the controller 230, signals are sent to a processor 240, which then controls movement of the clot removal instrument 300.

Figure 22:
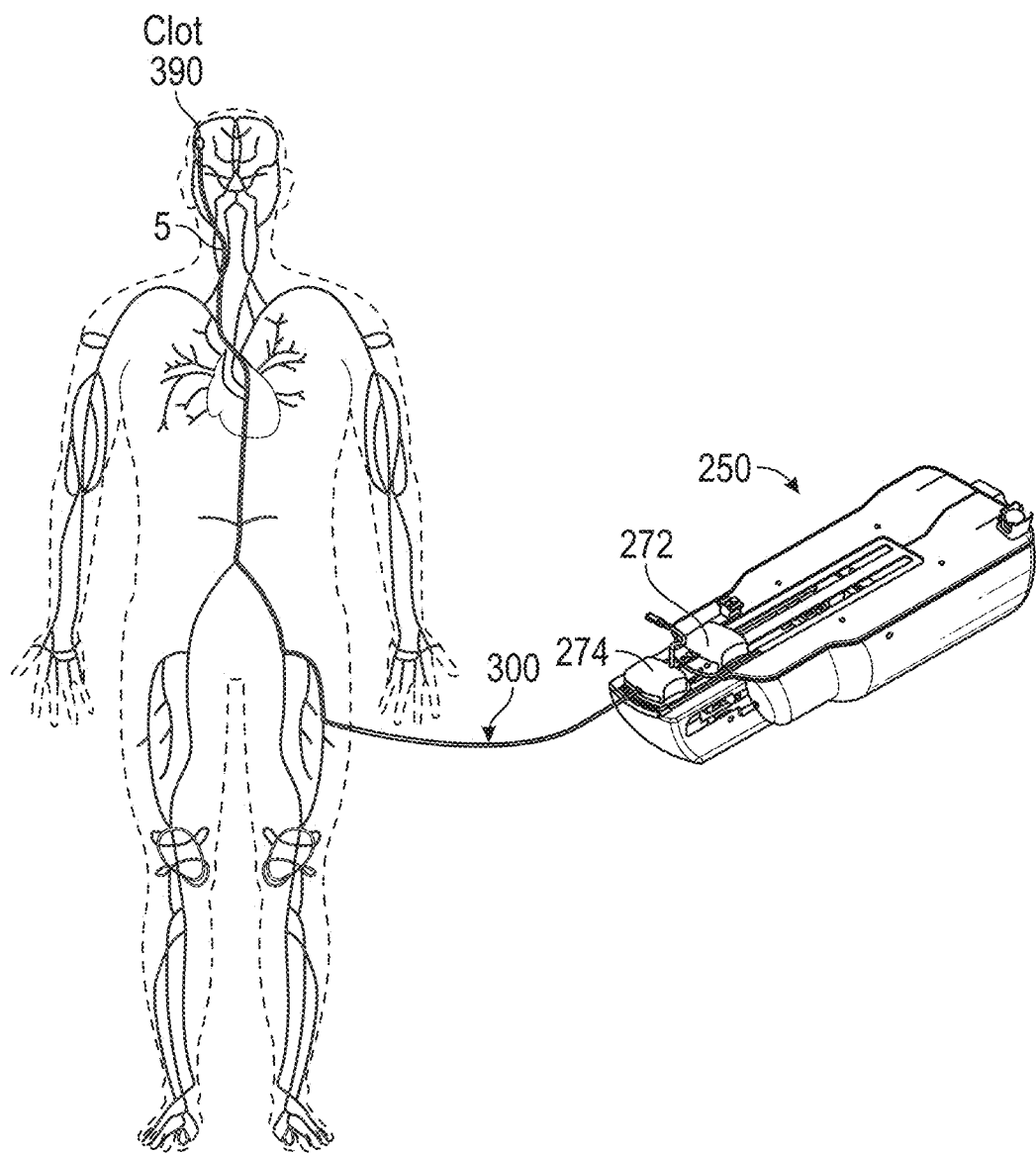
FIG. 22 illustrates a drive system of the robotic system of FIG. 21 for performing clot removal.

FIG. 22 illustrates a drive system 250 of the robotic system of FIG. 21 for performing clot removal within a patient's vasculature 5. As shown in this figure, the drive system 250 can be coupled to a clot removal instrument 300 via its proximal and distal handles 272, 274, which are capable of translating relative to one another (e.g., via a rail, track or virtually). The clot removal instrument 300 is configured to extend through an incision formed in the patient. In some embodiments, the clot removal instrument 300 enters into a patient via the groin or femoral artery, as shown in FIG. 22. In other embodiments, the clot removal instrument 300 enters into a patient radially or peripherally, such as through an incision along or near a patient's arm. The drive system 250 is capable of navigating the clot removal instrument 300 through vessels that can extend into the cerebrovasculature of the patient. As shown in FIG. 22, the vessels can reduce in size from the femoral region to the brain region. Advantageously, the clot removal instrument 300 is designed to have features for conveniently navigating vessels that reduce in size, as will be discussed further below.

Figure 23:
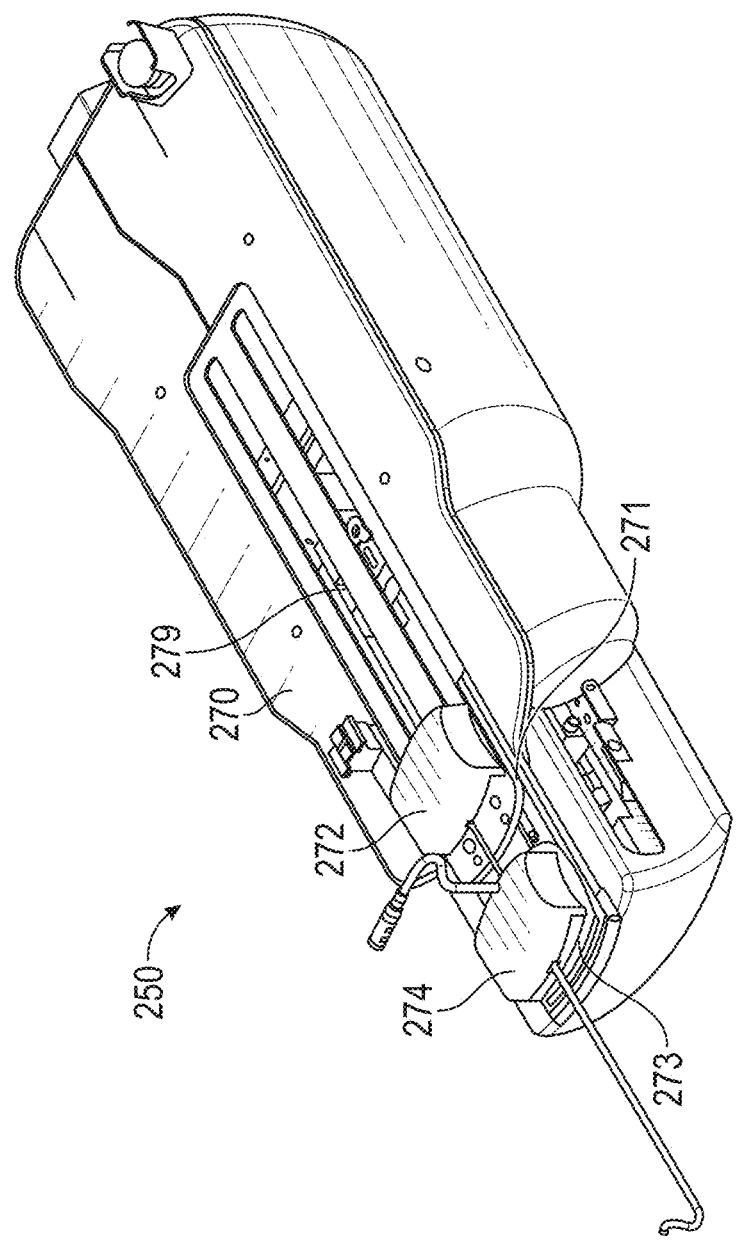
FIG. 23 illustrates a drive system of the robotic system of FIG. 21.

FIG. 23 illustrates a drive system 250 of the robotic system of FIG. 21. From this view, one can see the base 269 of the drive system 250 including a proximal instrument driver 271 for driving an elongated instrument attached to a proximal instrument splayer or handle 272 and a distal instrument driver 273 for driving an elongated instrument attached to a distal instrument splayer or handle 274. In some embodiments, the elongated instrument attached to the proximal instrument handle 272 comprises an aspiration catheter, while the elongate instrument attached to the distal instrument handle 274 comprises an access sheath through which the aspiration catheter translates. In other embodiments, the elongate instrument attached to the proximal instrument handle 272 comprises an access catheter, while the elongate instrument attached to the distal instrument handle 274 comprises an access sheath that is capable of telescoping relative to the access catheter to provide a conduit and/or working channel for other instruments that serve as a clot remover (e.g., a clot retriever, aspiration catheter, or other mechanical thrombectomy device). In some embodiments, a sterile adapter can be positioned between the proximal and distal instrument handles and their respective drivers.

In some embodiments, at least one of the proximal instrument driver 271 and the distal instrument driver 273 is capable of movement or translation. In some embodiments, both of the proximal instrument driver 271 and the distal instrument driver 273 are capable of movement or translation. In the present embodiment, the proximal instrument driver 271 is fixed, while the distal instrument driver 273 is capable of translation. As shown in FIG. 23, at least one of the proximal instrument driver 271 and the distal instrument driver 273 is capable of translation along a track or rail 279 of the drive system 250. In other embodiments, such as shown in FIG. 41, instrument drivers can be positioned on robotic arms that align along a virtual rail, such that there is no physical track or rail for translation.

Figure 41:
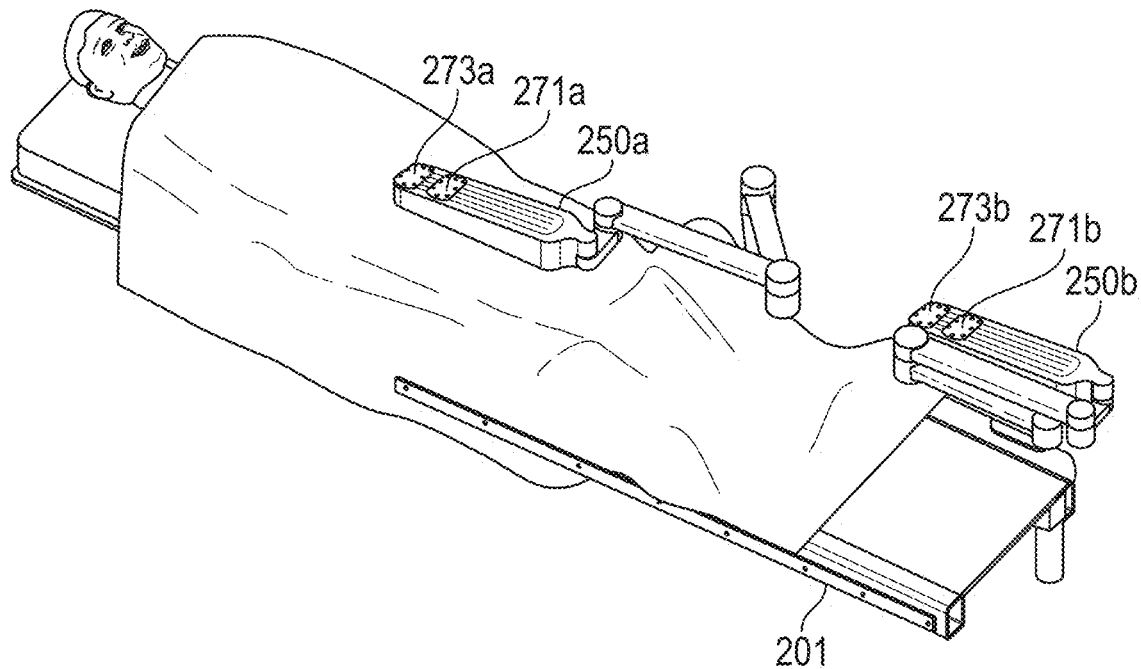
FIG. 41 illustrates an embodiment of a dual robotic system for performing clot removal.

FIG. 41 illustrates an embodiment of a dual robotic system 250a, 250b for performing clot removal. The dual robotic system 250a, 250b comprises a first robotic system 250a and a second robotic system 250b, each of which is similar to the robotic system 250 shown in FIG. 21. The first robotic system 250a includes a proximal instrument driver 271a for driving a first elongate member attached thereto and a distal instrument driver 273a for driving a second elongate member attached thereto. Similarly, the second robotic system 250b includes a proximal instrument driver 271b for driving a third elongate member attached thereto and a distal instrument driver 273b for driving a fourth elongate member attached thereto. Accordingly, by providing the dual robotic system 250a, 250b, more than two elongate members can be robotically controlled as part of a clot removal procedure. For example, in one embodiment, the distal instrument driver 273a can drive an access sheath, the proximal instrument driver 271a can drive an aspiration catheter within the access sheath, the distal instrument driver 273b can drive a clot disruptor within the aspiration catheter and the access sheath, and the proximal instrument driver 271b can drive a guidewire within the clot disruptor, aspiration catheter and access sheath. In other embodiments, while the dual robotic system 250a, 250b enables robotic control of at least four elongate members, in some embodiments, not all of the instrument drivers need be used. For example, in some embodiments, the dual robotic system 250a, 250b can utilize three of the four drivers 273a, 271a, and 273b to robotically control an access sheath, an aspiration catheter and a guide wire, without having to use the fourth driver.

Figure 42:
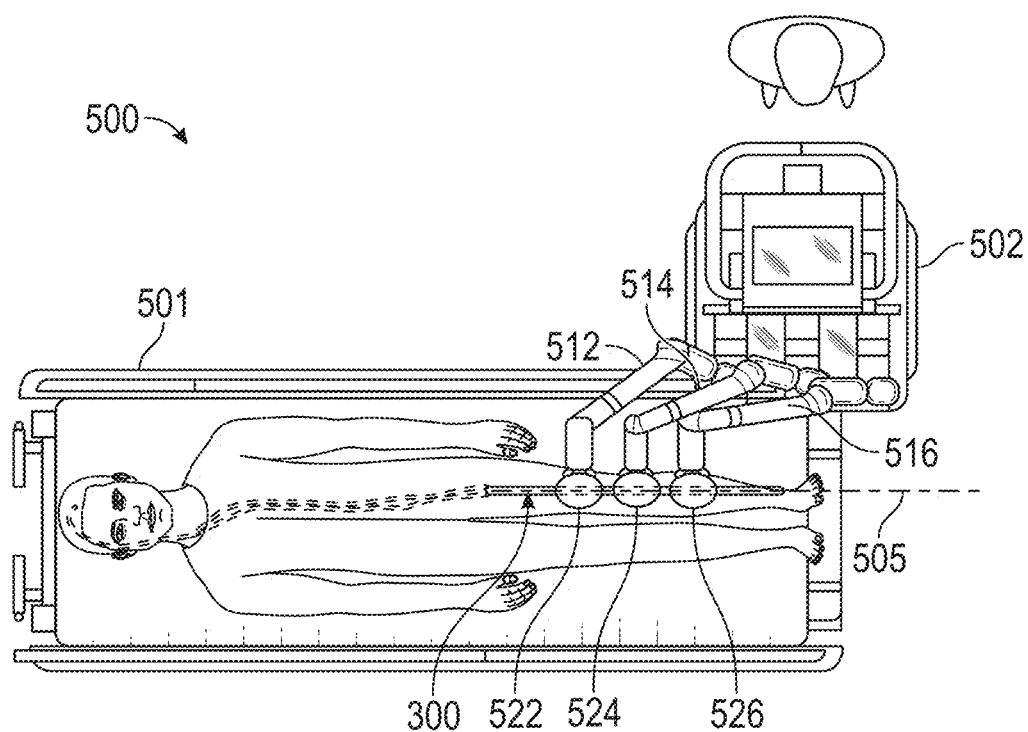
FIG. 42 illustrates an alternative embodiment of a robotic system for performing a clot removal.

FIG. 42 illustrates an alternative embodiment of a robotic system 500 for performing a clot removal. In the present embodiment, the robotic system 500 comprises a patient platform 501 (e.g., a bed) for receiving a patient thereon. A mobile cart 502 having one or more robotic arms 512, 514, 516 is capable of being positioned next to the patient platform 501. Each of the robotic arms 512, 514, 516 includes instrument drivers 522, 524, 526 that is capable of driving an elongate member attached thereto. For example, in the present embodiment, the robotic arms 512, 514, 516 are capable of driving different elongate members of a clot removal instrument 300 via the instrument drivers 522, 524, 526. In one embodiment, the robotic arm 512 and its associated instrument driver 522 are capable of positioning and driving an access sheath, the robotic arm 514 and its associated instrument driver 524 are capable of positioning and driving an aspiration catheter within the access sheath, and the robotic arm 516 and its associated instrument driver 526 are capable of positioning and driving a clot disruptor or guidewire within the aspiration catheter and the access sheath. In some embodiments, the instruments drivers 522, 524, 526 can be aligned via a "virtual rail" in which the robotic arms 512, 514, 516 position them in alignment.

Advantageously, as the cart 502 is mobile, it is capable of being moved to different positions relative to the patient. For example, the cart 502 can be positioned such that the robotic arms 512, 514, 516 can perform a clot removal through a femoral artery of the patient. The cart 502 can also be positioned such that the robotic arms 512, 514, 516 can perform a clot removal through a radial or peripheral entry of the patient on or near an arm of the patient. In addition, one skilled in the art will appreciate that the cart 502 can include less than (e.g., 2 or less) or more than (e.g., 4 or more) three arms. In addition, a clot removal procedure can be performed using a pair of carts with multiple arms, or using a cart combined with a laparoscopic bed having multiple arms, as described below.

Figure 43:
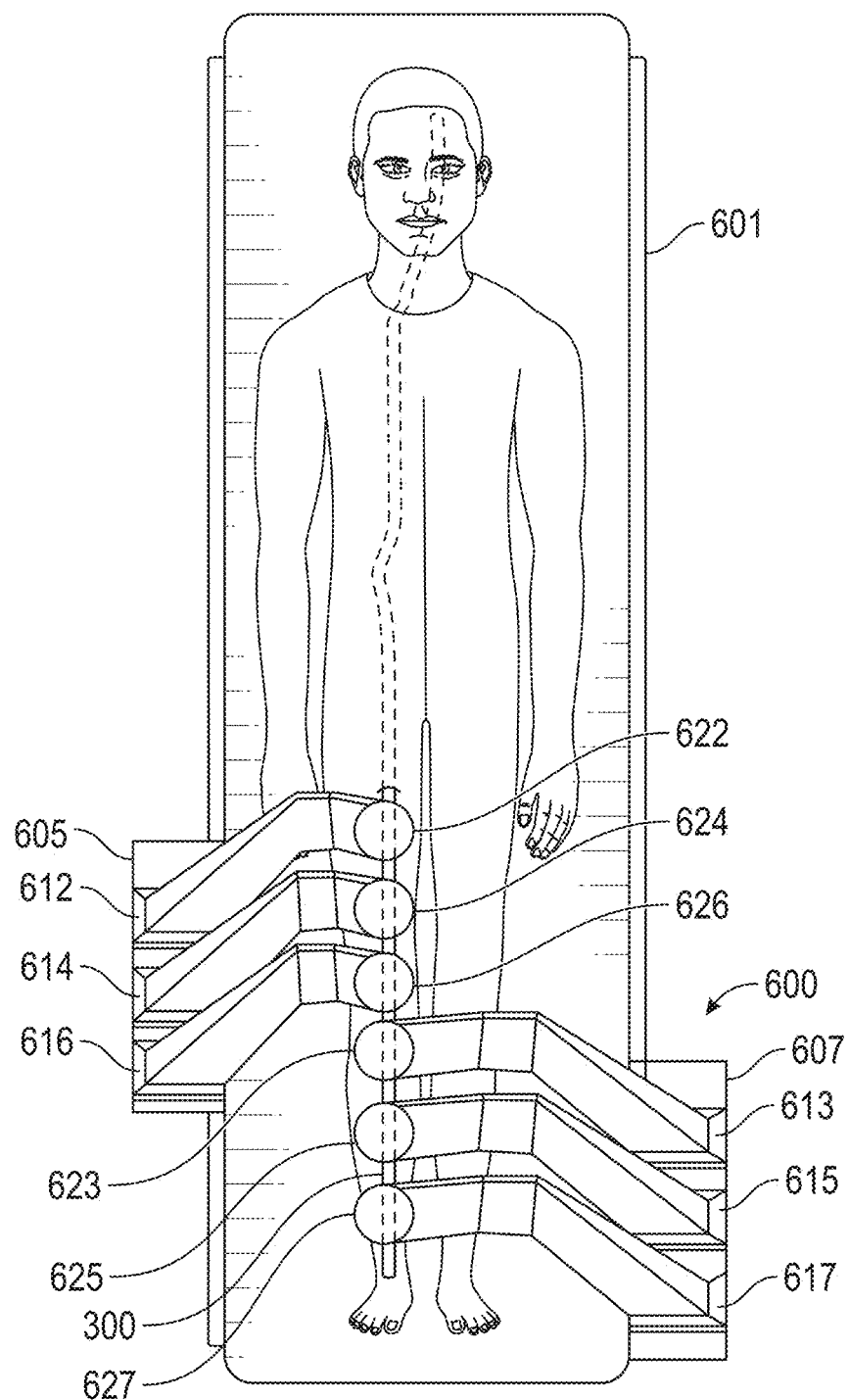
FIG. 43 illustrates a yet another alternative embodiment of a robotic system for performing a clot removal.

FIG. 43 illustrates a yet another alternative embodiment of a robotic system 600 for performing a clot removal. The robotic system 600 comprises a plurality of robotic arms 612, 614, 616, 613, 615, 617 that are each coupled to an adjustable arm support 605, 607 similar to those described in FIGS. 12 and 13. As shown in the figure, the robotic system 600 comprises six robotic arms, in which three 612, 614, 616 are coupled to a first adjustable arm support 605 and another three 613, 615, 617 are coupled to a second adjustable arm support 607. Each of the robotic arms 612, 614, 616, 613, 615, 617 is respectively coupled to an instrument driver 622, 624, 626, 623, 625, 627 that is optionally coupled to a sterile adapter. The instrument drivers 622, 624, 626, 623, 625, 627 are each capable of attachment to a handle of an instrument, thereby allowing for driving and articulation of the instrument.

As the robotic system 600 includes six robotic arms, there can advantageously be up to six instruments of an instrument system 300 that can be advantageously controlled. The instruments can include various types of elongate members, including but not limited to one or more access sheaths, clot removal catheters (e.g., aspiration catheters, stent deployment catheters), clot disruptors (e.g., including mechanical disruptors and energy disruptors), laser catheters, water jet catheters, and guide wires. One skilled in the art will appreciate that not all of the arms of the robotic system 600 need to be used, but that the system provides the option to use all if recommended by a physician. For example, in one embodiment, five of the robotic arms can be used, with the first robotic arm 612 used to control an wide access sheath (e.g., one that stops at or near the femoral artery), a second robotic arm 614 used to control a narrower access sheath (e.g., one that stops at or near the carotid artery), a third robotic arm 616 used to control a clot removal catheter (e.g., capable of moving beyond the carotid artery if needed), a fourth robotic arm 613 used to control a clot disruptor to reduce the size of the clot, and a fifth robotic arm 615 used to control a guidewire.

In an alternative embodiment, one of the arms can be used to stabilize an instrument system 300 as it is being inserted into a patient. For example, in one embodiment, first robotic arm 612 can be used to stabilize an instrument system 300 as it is inserted through a femur or radially. In some embodiments, the first robotic arm 612 can serve as and/or be coupled to an introducer that allows for stabile insertion of the instrument system 300 through an incision. In such an embodiment in which the first robotic arm 612 is used as an instrument stabilizer, the second robotic arm 614 can be used to control a wide access sheath (e.g., one that stops at or near the carotid artery), the third robotic arm 616 can be used to control a narrower access sheath (e.g., one that stops at or near the carotid artery), a fourth robotic arm 613 can be used to control a clot removal catheter (e.g., capable of moving beyond the carotid artery if needed), a fifth robotic arm 615 can be used to control a clot disruptor to modify the clot, and a sixth robotic arm 617 can be used to control a guidewire. Thus, the availability of multiple arms, such as six or more, certainly increases the options for use for a clinician or physician.

In the present embodiment, the robotic arms 612, 614, 616 are coupled to a first adjustable arm support 605, while the robotic arms 613, 615, 617 are coupled to a second adjustable arm support 607. Each of the arm supports 605, 607 resides on opposing sides of the patient, such that the procedure can be performed bilaterally. Both the first set of robotic arms 612, 614, 616 and the second set of robotic arms 613, 615, 617 are capable of translating relative to one another. Each of the robotic arms can move in multiple degrees of freedom (e.g., six, seven, eight or more), which advantageously helps to avoid collisions between one another.

The robotic systems described herein can be found in hospital and emergency centers. Advantageously, at least some of the systems are mobile such that they can be transported into different rooms. In addition, the robotic systems described herein can also be incorporated into a mobile vehicle, such as an emergency vehicle. This can be particularly useful to patients that may need immediate care that are not close to an emergency center, such as patients in rural areas.

One skilled in the art will appreciate that the robotic systems described herein are not limited to performing clot removal. For example, the system shown and described in FIG. 43 can also be used to perform a concomitant endoscopic and laparoscopic procedure, such as an escalated colon polyp resection. Accordingly, the robotic systems described herein provide great versatility in performing various types of surgeries beyond those described in detail herein. In addition, the robotic systems described herein can be used to treat various maladies, including stroke, myocardial infarction, cardiac arrest, or other types medical issues.

B. Instrument Systems for Clot Removal.

This section describes various types of instrument systems that can be used for clot removal. While the devices described herein may be referred to as "instruments systems," as they often include multiple elongate members that may be independently controlled from one another, one skilled in the art can appreciate that they can also be considered simply as "instruments" having multiple independently controlled components. These instrument systems can include one or more elongate members that can be robotically operated, navigated, and/or articulated using any of the systems described herein, such as shown in FIGS. 23, 41, 42, and 43.

In some embodiments, an instrument system can include multiple elongate members. For example, in one embodiment, an instrument system includes a first elongate member comprising an access sheath, a second elongate member comprising a clot removing (e.g., aspiration) catheter, a third elongate member comprising a clot modifier (e.g., disruptor), and a fourth elongate member comprising a guide wire.

At least one or more of the elongate members of the instrument systems can include one or more drive or articulating wires. In some embodiments, one or more elongate members can include four articulating wires. These articulating wires can be spaced evenly relative to one another about a circumference of the elongate member. In other embodiments, one or more of the elongate members can include less than four articulating wires (e.g., such as a three, two or a single articulating wire). By having a relatively small number of articulating wires, this allows an elongate member to have a reduced diameter, which can be advantageous for robotically navigating smaller and smaller vessels.

Figure 24:
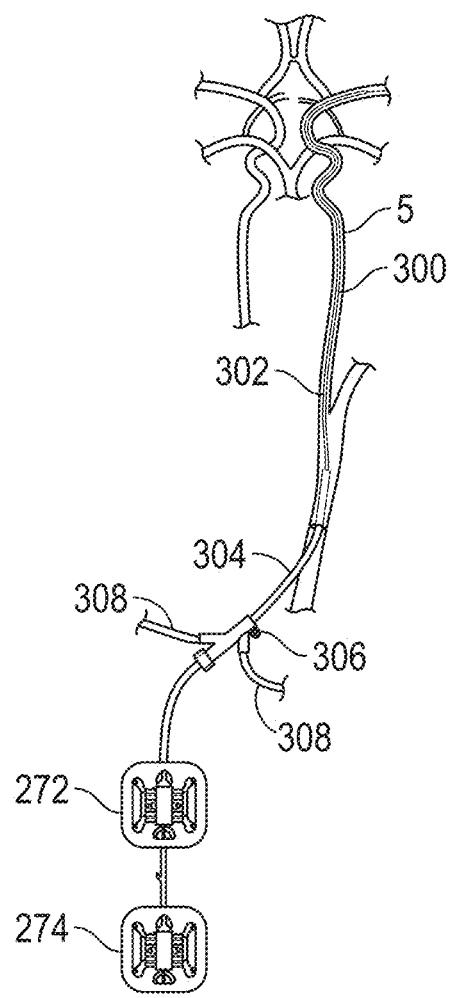
FIG. 24 illustrates an instrument system for performing clot removal.

FIG. 24 illustrates an instrument system 300 for performing clot removal. The instrument system 300 comprises a first elongate member 304 (e.g., an access sheath) and a second elongate member 302 (e.g., a clot removing catheter such as an aspiration catheter) that extends through a lumen of the first elongate member 304. The first elongate member 304 is coupled to the distal instrument handle 274, while the second elongate member 302 is coupled to the proximal instrument handle 272. The distal instrument handle 274 is configured to articulate the first elongate member 304 via one or more pull or articulating wires, while the proximal instrument handle 272 is configured to articulate the second elongate member 302 via one or more pull or articulating wires. The distal instrument handle 274 and proximal instrument handle 272 are configured to removably attach to distal and proximal instrument drivers 273, 271 including motors, drive shafts, and sensors (e.g., torque sensors) as discussed above. These instrument drivers 273, 271 can be found in any of the systems described herein, as shown in FIGS. 23, 41, 42, and 43.

In some embodiments, the first elongate member 304 comprises an access sheath. The access sheath serves as a guide that can be parked anywhere along a vessel that leads into cerebrovasculature of the patient. For example, in some embodiments, the first elongate member 304 comprises an access sheath that can be parked at or near the carotid artery, thereby serving as a conduit for even smaller elongate members to access cerebrovasculature. In some embodiments, the first elongate member 304 comprises one or more pull or articulating wires to articulate the first elongate member 304 through tortuous anatomy.

In some embodiments, the second elongate member 302 comprises a clot removing catheter such as an aspiration catheter. The second elongate member 302 can be used to retain a clot via vacuum or suction. Upon aspiration, the second elongate member 302 can then be retracted back and out through the vascular system of the patient, thereby removing the clot from the patient. In some embodiments, the second elongate member 302 is capable of moving within a lumen of the first elongate member 304. Accordingly, the second elongate member 302 can have a diameter that is less than a diameter of the first elongate member 304 such that it can telescope in and out of the first elongate member 304. Like the first elongate member 304, the second elongate member 302 comprises one or more pull or articulating wires to articulate the second elongate member 304 through tortuous anatomy. In some embodiments, the first elongate member 304 and the second elongate member 302 each share an equal number of pull or articulating wires. In other embodiments, the first elongate member 304 and the second elongate member 302 each have a different number of pull or articulating wires. For example, the first elongate member 304 can have a greater number of pull wires (e.g., up to four) than the second elongate member 302 (e.g., up to two). This advantageously allows the second elongate member 302 to have a lesser diameter such that it can navigate even smaller tortuous vessels than the first elongate member 304.

As shown in FIG. 24, a hub 306 can be coupled to one or more of the first elongate member 304 and second elongate member 302. The hub 306 comprises one or more lines 308 for performing suction or irrigation via the first and/or second elongate members 304, 302. In some embodiments, the one or more lines 308 can be attached to a pump for providing suction capabilities by the first and/or second elongate members 304, 302.

Figure 25:
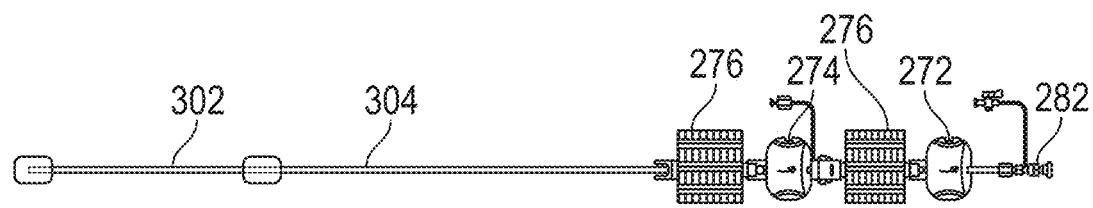
FIG. 25 illustrates an alternative embodiment of an instrument system for performing clot removal.

FIG. 25 illustrates an alternative embodiment of an instrument system 300 for performing clot removal. The instrument system 300 is similar to the system in FIG. 24 in that it includes a distal instrument handle 274 coupled to a first elongate instrument (e.g., an access sheath 304) and a proximal instrument handle 272 coupled to a second elongate instrument (e.g., a clot removal catheter 302 that travels through the access sheath 304). In the present embodiment, however, the instrument system 300 further comprises one or more anti-buckling devices 276 positioned adjacent the instrument handles 274, 272. The anti-buckling devices 276 advantageously reduce the risk of buckling that can occur as an elongate member is fed through a patient. In some embodiments, one or more of the anti-buckling devices 276 can be replaced with a feed roller that helps to feed an elongate member into the patient. In some embodiments, the anti-buckling devices 276 advantageously provide for stabilization of the instrument system 300 upon insertion into an incision (e.g., via the femur or radially).

Figure 26:
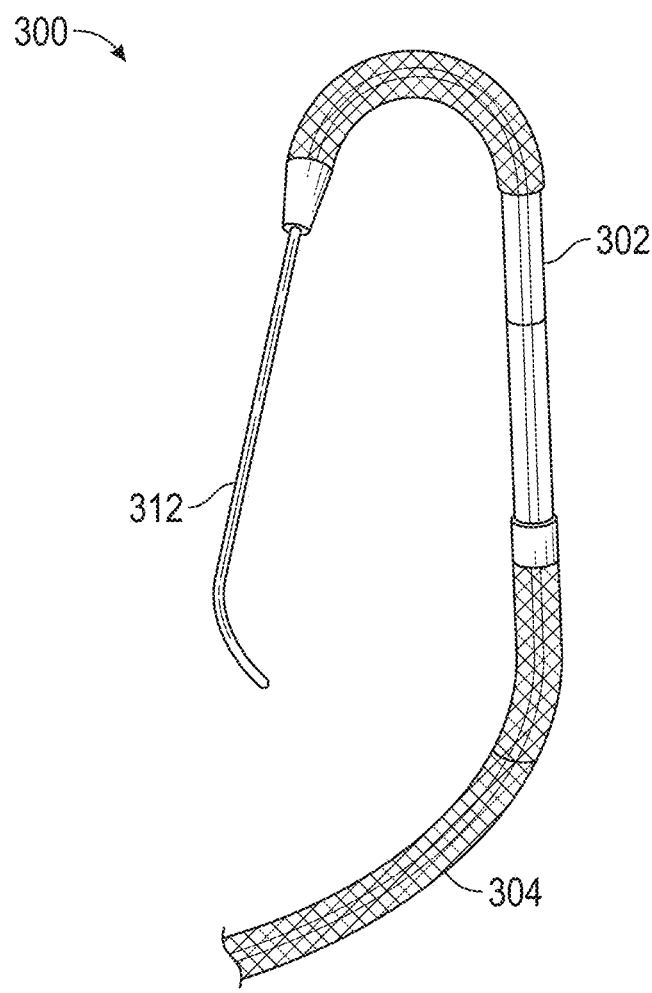
FIG. 26 illustrates a catheter instrument for performing clot removal.
Figure 27:
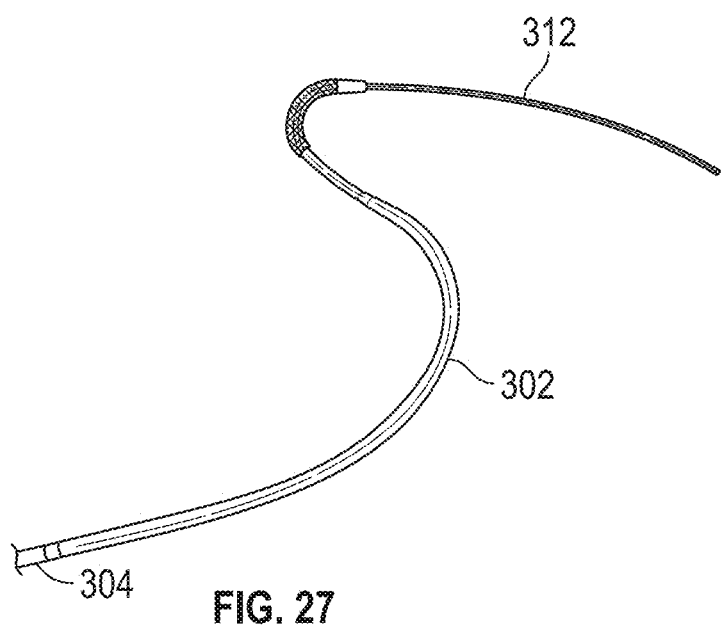
FIG. 27 illustrates a different front perspective view of the catheter instrument of FIG. 26.

FIG. 26 illustrates a catheter instrument 300 for performing clot removal. FIG. 27 illustrates a different front perspective view of the catheter instrument 300 of FIG. 26. The catheter instrument 300 comprises a plurality of elongate members including an access sheath 304, a clot removal catheter 302, and a clot disruptor 312. A guide wire, which can be guided through the clot disruptor 312, is not shown. In some embodiments, each of these elongate members is controlled robotically. In some embodiments, only some of the elongate members is controlled robotically, while others can be controlled manually. For example, in some embodiments, the access sheath 304 and the clot removal catheter 302 can be robotically and telescopically controller, while the clot disruptor 312 and the guide wire can controlled manually. In other embodiments, only the guide wire can be delivered robotically, while the access sheath 304, clot removal catheter 302, and clot disruptor 312 can be delivered manually thereover.

The access sheath 304 comprises an elongate member that is capable of insertion through a femoral artery. The access sheath 304 is configured to serve as a conduit for one or more elongate members that are received therein, including the clot removal catheter 302 and the clot disruptor 312. The access sheath 304 comprises a flexible shaft or tube that can be formed at least in part by a braided structure. In some embodiments, the access sheath 304 comprises nylon with a stainless steel braid. The access sheath 304 is advantageously capable of having both structure and flexibility to maneuver through different vessels of a patient.

The clot removal catheter 302 comprises an elongate member that is capable of telescoping through the access sheath 304. In some embodiments, the clot removal catheter 302 comprises an aspiration catheter for aspirating and suctioning a clot therein. In some embodiments, the clot removal catheter 302 can be coupled to a stent, net, basket, or other 3-D structure (shown in FIG. 29A) that is capable of physically capturing a clot therein for removal. In some embodiments, rather than serving as a clot remover, the catheter 302 can be used to administer thrombolytics (e.g., streptokinase, urokinase, tPA) and/or other anticoagulants to help break down clots via drug administration. In other words, one or the objectives of the clot removal catheter 302 is to provide reperfusion of an affected vessel by mechanical thrombectomy, administration of thrombolytics, or any combination thereof. Like the access sheath 304, the clot removal catheter 302 advantageously has both structure and flexibility to maneuver through different vessels of a patient. In some embodiments, the clot removal catheter 302 can also be formed in part of polymer that is coupled to a stainless steel braid.

In embodiments in which the clot removal catheter 302 is an aspiration catheter, the clot removal catheter 302 can be coupled to an aspiration pump (not shown). The pump can be coupled to a flow meter to control the amount of pressure provided to the clot removal catheter 302. In some embodiments, the clot removal catheter 302 can be controlled to a feedback loop in a processor (e.g., 240 in FIG. 21) that constantly monitors and maintains an appropriate pressure in the clot removal catheter 302. In addition, such a processor 240 can be used to determine whether the clot removal catheter 302 should be used for one function (e.g., aspiration) or another (e.g., irrigation).

The clot disruptor 312 comprises an elongate member that is capable of maneuvering through the lumens of the clot removal catheter 302 and access sheath 304. The clot disruptor 312 can be used to modify a clot to make it easier for removal by the clot removal catheter 302. For example, in some embodiments, the clot disruptor 312 comprises a shaft that is capable of piercing through a clot. The shaft can be coupled to an optional disruptor or cutter 312 (e.g., a dull blade or propeller). The shaft is capable of rotation such that the clot can be modified or disrupted, thereby reducing the clot to smaller particles. In some cases, this can make a clot easier to be removed by the clot removal catheter 302. In some embodiments, the clot disruptor 312 can be formed of stainless steel or nitinol. The clot disruptor 312 can have a blunt distal tip so as to pass through a clot with minimal risk of harm to a patient's vessel, thereby advantageously reducing the risk of inadvertent vessel scraping.

A guidewire (not shown in FIG. 26) capable of insertion into a patient's vasculature can also be part of the instrument 300. The guidewire can be inserted either manually or robotically, with one or more of the access sheath 304, clot removal catheter 302, and/or the clot disruptor 312 being delivered thereover. In some embodiments, the guidewire can be formed of a thin, flexible biocompatible material, such as stainless steel or nitinol, and can serve as a guide to target clot of the patient.

Figure 28:
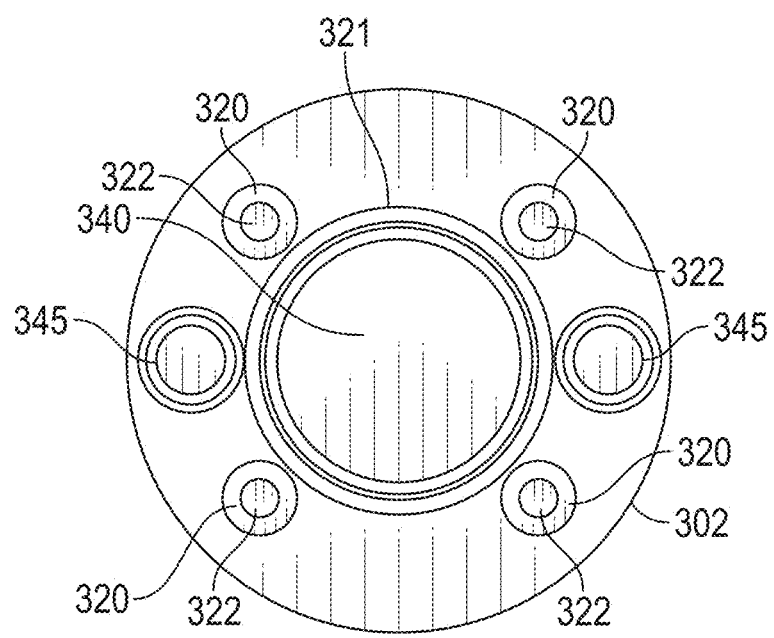
FIG. 28 illustrates a cross-sectional view of a sheath or catheter of the catheter instrument of FIG. 26.

FIG. 28 illustrates a cross-sectional view of an elongate member of the catheter instrument 300 of FIG. 26. The cross-sectional view can be representative, for example, of a cross-section of the access sheath 304. From this view, one can see how the elongate member comprises a working lumen or channel 340 for guiding one or more catheters or instruments therethrough. While in the present embodiment, the working channel 340 is illustrated as having a singular circular cross-section, in other embodiments, the working channel 340 can have a cross-section that is oval in shape. In some embodiments, the working channel 340 can be of a dual connecting oval with a narrower width between them.

The elongate member comprises one or more drive or articulating cables or wires 322. In the present embodiment, the elongate member comprises four articulating wires 322 that are distributed about a circumference of the elongate member. In some embodiments, the four articulating wires 322 are distributed approximately 90 degrees from one another. The articulating wires 322 can be received within coil pipes 320. While in the present embodiment, the elongate member includes four articulating wires 322, in other embodiments, the elongate member can include less than four articulating wires 322, such as three, two, one or none at all. By minimizing the number of articulating wires 322, this can be particularly helpful for maintaining a smaller diameter for elongate members that are used to navigate smaller vessels (e.g., in the cerebrovasculature). Accordingly, one skilled in the art will appreciate that the cross-sectional view of the elongate member in FIG. 28 is representative of one possible embodiment, and that other embodiments may include a different number of articulating wires 322.

The elongate member further comprises a pair of sensors 345. In some embodiments, the sensors 345 can comprise EM sensors that can be used, for example, to detect and measure roll of the elongate member. In some embodiments, one or more of the elongate members can include a sensor that can be used to identify concentricity within a vessel during navigation (e.g., via ultrasound), as discussed below with respect to FIG. 33B. In some embodiments, in addition to or in place of the sensors 345, the elongate member can comprise one or more shape sensing fibers. The shape sensing fibers can be used to provide localization information for an elongate member as it travels through the patient's vasculature.

In the present embodiment, the elongate member comprises a spine 321 that serves as a backbone for the elongate member. In some embodiments, the spine can be formed of a biocompatible material such as nitinol. In some embodiments, the elongate member comprises one or more braided features that extend along a length of the elongate member.

Figure 29A:
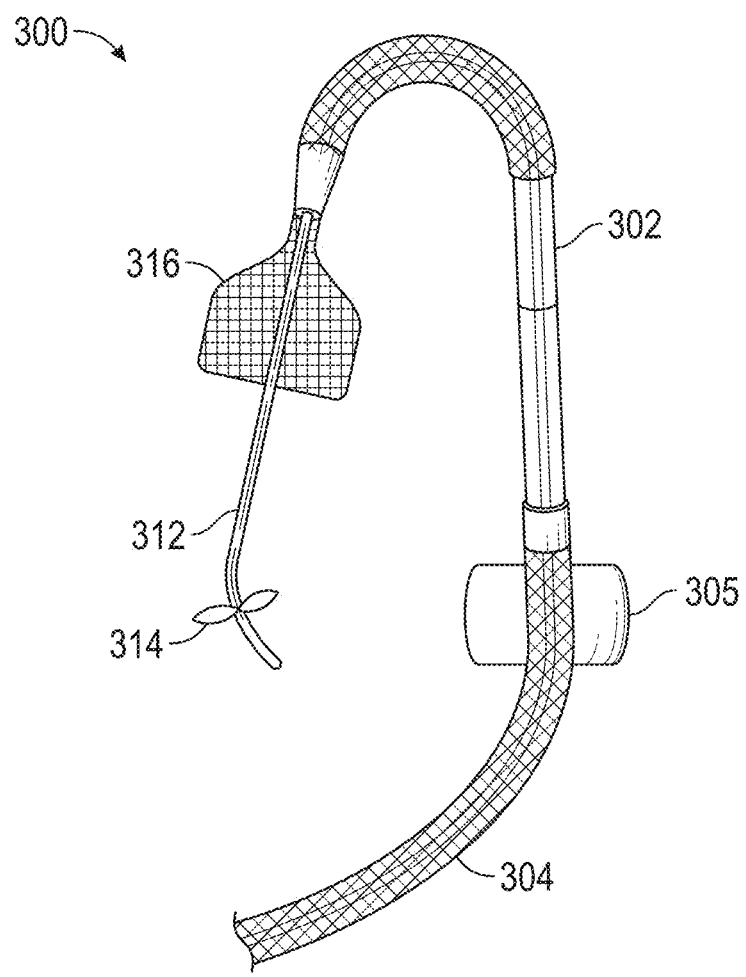
FIG. 29A illustrates an alternative embodiment of a catheter instrument for performing clot removal including an inflation member.

FIG. 29A illustrates an alternative embodiment of a catheter instrument 300 for performing clot removal including an inflation member 305. The catheter instrument 300 is similar to the catheter instrument shown in FIG. 26 in that it includes an access sheath 304, a clot removal catheter 302 and a clot disruptor 312. In the present embodiment, however, the catheter instrument 300 includes additional features, including an inflatable member 305 for vessel occlusion, a 3-D structure 316 for clot retrieval, and a clot cutter 314.

In the illustrated embodiment, the catheter instrument 300 comprises an inflatable member 305 that is coupled to the outer body of the access sheath 304. The inflatable member 305 is capable of inflation to thereby occlude a vessel. The advantage of the inflatable member 305 is that it can stabilize the catheter instrument 300 within a patient's vasculature, such that it allows for one or more elongate members to be delivered accurately and with precision. In some embodiments, the inflatable member 305 comprises a balloon that can be expanded to occlude a vessel.

In the illustrated embodiment, the catheter instrument 300 further comprises a 3-D structure 316, such as a stent, net, basket, or retriever that is used to capture a clot. In some embodiments, the 3-D structure 316 is coupled to the clot removal catheter 302, and can be deployed via a physician. In other embodiments, the 3-D structure 316 is coupled to the clot disruptor 312 and can be deployed as the clot disruptor 312 is moved far enough out of the clot removal catheter 302.

In the illustrated embodiment, the catheter instrument 300 further comprises a clot modifier or disruptor 312 that includes a clot manipulator in the form of a propeller or cutter 314. The cutter 314 can help to disrupt a clot and to turn it into smaller particles if desired. In some embodiments, the clot disruptor 312 is capable of rotation, thereby causing disruption of the clot structure.

Figure 29C:
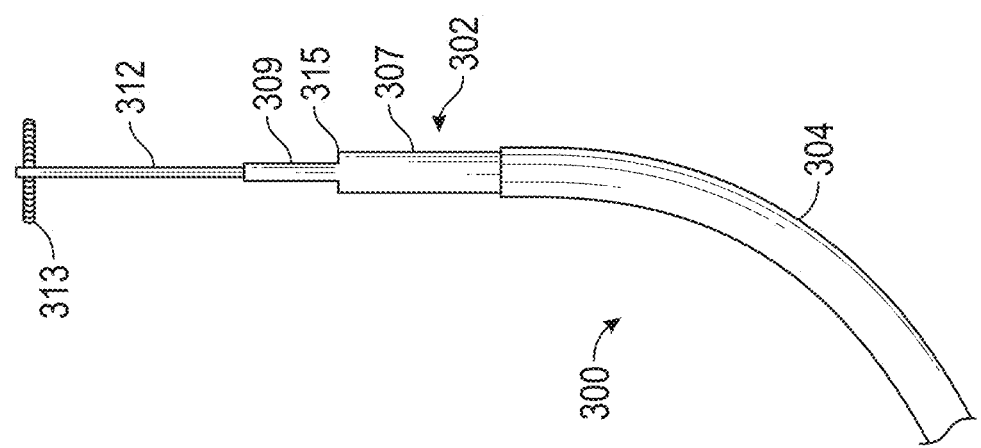
FIG. 29C illustrates an alternative embodiment of a catheter instrument for performing clot removal including a dual lumen catheter.
Figure 29B:
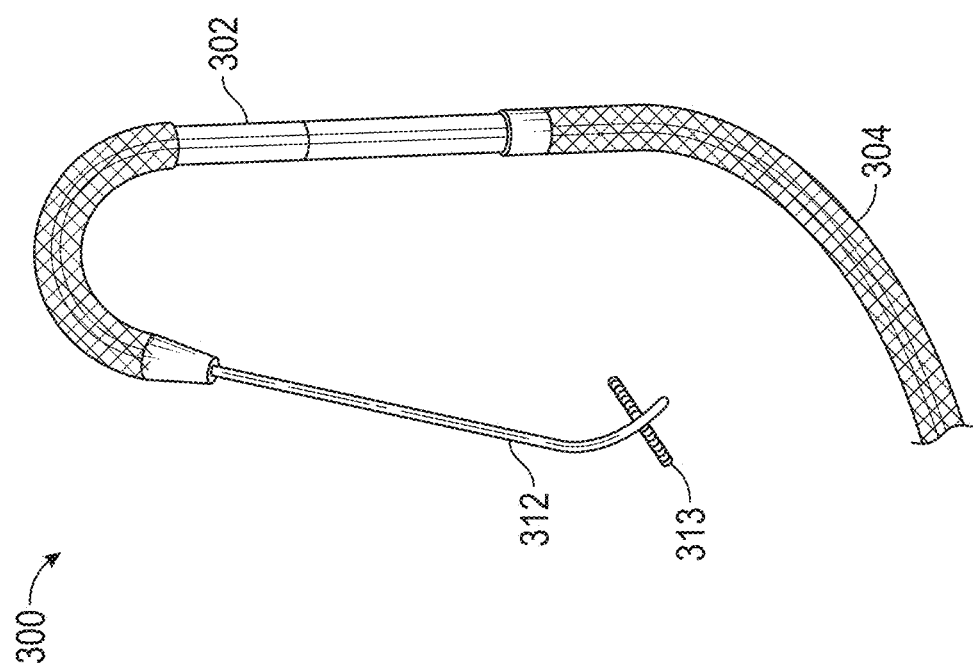
FIG. 29B illustrates an alternative embodiment of a catheter instrument for performing clot removal including a distal protector.

FIG. 29B illustrates an alternative embodiment of a catheter instrument 300 for performing clot removal including a distal protector 313. The catheter instrument 300 is similar to the catheter instrument in FIG. 26 in that it includes an access sheath 304, a clot removal catheter 302 and a clot disruptor 312. In the present embodiment, however, the clot disruptor 312 is coupled to a multi-functional distal guard 313. The distal guard 313 can serve multiple functions. First, it can be used to protect clot material from being distributed downstream from the catheter instrument 300. This advantageously helps prevent loosened clot material from flowing beyond the distal guard 313, thereby reducing the risk of subsequent strokes from occurring. Second, the distal guard 313 can be used to retrieve the clot back towards the clot removal catheter 302. This can help, for example, in the event that a clot is positioned too far from aspiration by the clot removal catheter 302. In this event, the clot disruptor 312 can be used to pierce a clot, whereby the distal guard 313 can be deployed or inflated beyond the clot. As the clot disruptor 312 is retracted through the clot removal catheter 302, the distal guard 313 helps to physical move any clot material back towards the clot removal catheter 302. One skilled in the art will appreciate that the distal guard 313 can be attached to any of the instruments described within this application, and is not limited to the embodiment of FIG. 29B.

FIG. 29C illustrates an alternative embodiment of a catheter instrument 300 for performing clot removal including a dual lumen catheter. The catheter instrument 300 is similar to the catheter instrument in FIG. 26 in that it includes an access sheath 304, a clot removal catheter 302 and a clot disruptor 312. The catheter instrument 300 also includes a distal guard 303 coupled to the clot removal catheter 302, as described with respect to FIG. 29B. In the present embodiment, however, the clot removal catheter 302 is in the form of a dual-lumen comprised of a first lumen 307 of a first diameter and a second lumen 309 of a second diameter separated by a valve 315. By providing these different lumens 307, 309, the aspiration capabilities of the clot removal catheter 302 can be modified, and in some cases, enhanced relative to a single lumen catheter. In some embodiments, the clot removal catheter 302 can be viewed as having a tapered tip separated by a wider proximal lumen.

The catheter instruments 300 described herein can be used with any of the systems described above. As noted above, in some embodiments, each of the elongate members of the instruments 300 can be robotically controlled, while in other embodiments, some of the elongate members can be robotically controlled while some of the elongate members can be manually controlled.

C. Navigation and Imaging Systems for Clot Removal.

Below are various imaging and navigation systems that can accompany any of the systems and instruments described above. Advantageously, many of these imaging and navigation systems can be used not only with robotically-controlled instruments (such as those described above), but can also be used to better guide and navigate non-robotically controlled (e.g., manual) instruments through tortuous vessels.

Improved imaging systems and methods can be provided to assist in the navigation of one or more clot removal instruments. The imaging systems can take images both pre-procedurally and during a procedure to help aid in the navigation of a clot removal instrument.

Figure 30A:
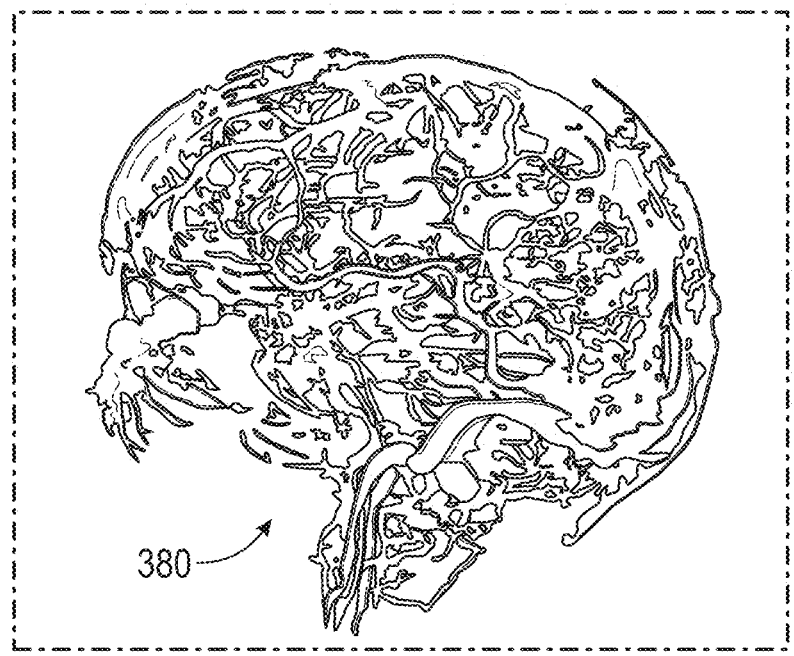
FIG. 30A illustrates a 3-D model that can be generated using pre-operational images.
Figure 30B:
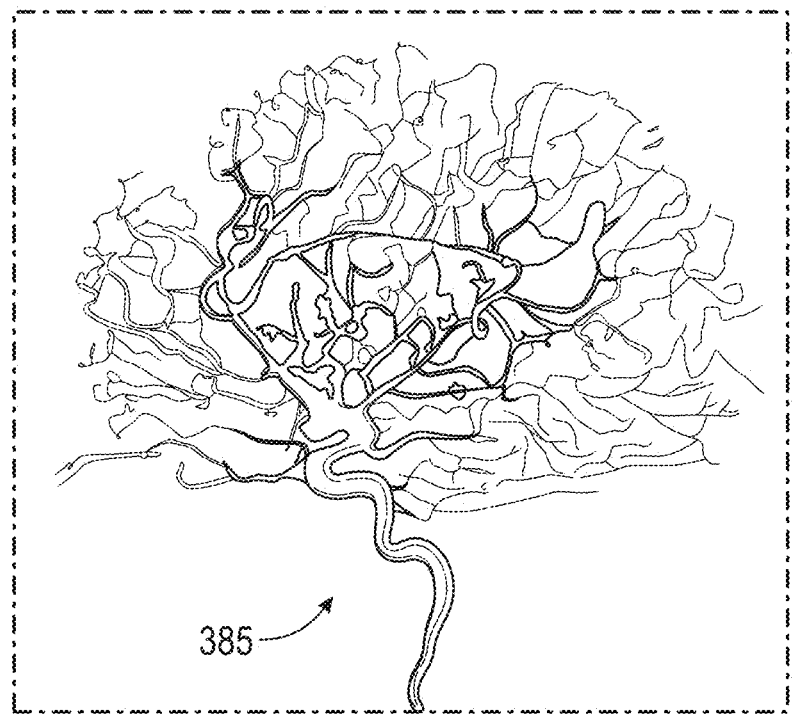
FIG. 30B illustrates an example pre-operational image that can be used to generate a 3-D model.

FIG. 30A illustrates a 3-D model 380 that can be generated using pre-operational or pre-procedure images. FIG. 30B illustrates an example pre-operational image 385 that can be used to generate a 3-D model. Pre-procedural imaging can be done by one or more of computerized tomography (CT), CT angiography (CTA), magnetic resonance angiography (MRA), or fluoroscopy. In an embodiment that uses multiple pre-procedural imaging approaches, a physician can switch the source of his/her navigation from one imaging approach to another (e.g., switch between CT-based navigation to CTA-based navigation). In another embodiment, navigation software can combine pre-procedural image data from multiple approaches to improve the quality and amount of information that is displayed to a clinician or physician. This can include creating a manipulatable 3-D reconstruction of vasculature from the images. In FIG. 30A, a 3-D model or reconstruction 380 of vasculature that has been generated from one or more imaging scans (e.g., fluoroscopy, CT, CTA, or MRA), such as the image 385 shown in FIG. 30B. Once a 3-D reconstruction 380 of vasculature has been created, a clinician or physician can utilize the 3-D reconstruction 380 to navigate through tortuous vessels leading up to and through the cerebrovasculature.

In some embodiments, an occlusion site (e.g., location of a clot) can be identified on the 3-D model or reconstruction of the vasculature. In some embodiments, the occlusion site can be optionally identified via software and added to the 3-D model. In some embodiments, identification of the occlusion site is performed by a physician in a pre-procedural planning step. In other embodiments, identification of the occlusion site is performed automatically by software with little or no help from the physician. As it is crucial to identify an occlusion site, particularly during an acute ischemic stroke, there can be significant value in using software to automate the location of an occlusion site.

The 3-D model (such as the model 380 shown in FIG. 30A), which can include an optional occlusion site, can be available for viewing on a screen by a clinician or physician. For example, the 3-D model can be viewed on a screen 210 of a console 220 as shown, for example, in FIG. 21. In addition to the 3-D model 380 shown in FIG. 30A, additional virtual models can be generated and displayed on the same or different screen of a console, such as those shown in FIGS. 31 and 32.

Figure 31:
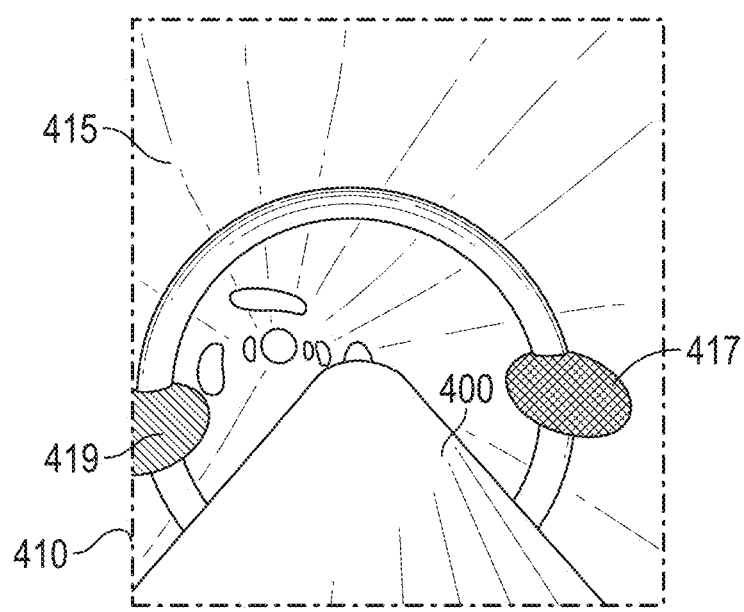
FIG. 31 illustrates a first-person view of a generated model of a vessel.

FIG. 31 illustrates a first-person view 410 of a generated model of a vessel 415. The generated model can be constructed using any of the imaging modalities described above, and includes a model of a vessel 415 viewed from a first-person. From this view, a physician can navigate a clot removal instrument from a current location to an occlusion site. From this first-person view 410, one can see a virtual, generated model of a catheter 400 as it is being driven into a virtual, generated model of vessel 415. An optional ring indicator that includes a right marker 417 and a left marker 419 of different colors can be provided. The optional right and left markers 417, 419 advantageously assist a clinician or physician that is controlling the instrument (e.g., via a controller or pendant) to know which way to steer and/or navigate the instrument within the vessel.

Figure 32:
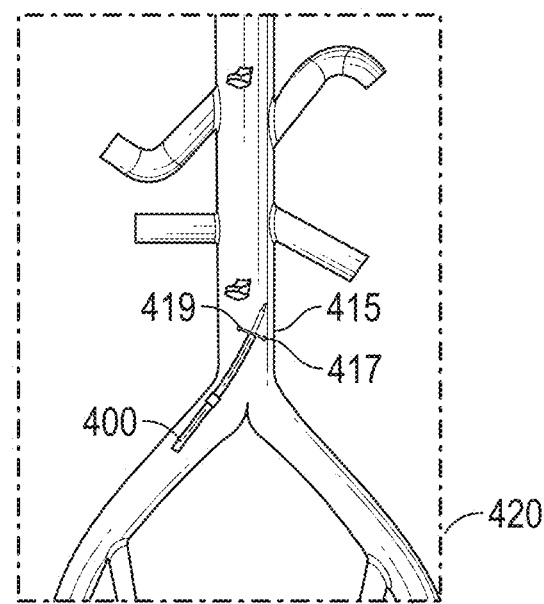
FIG. 32 illustrates a third-person view of a generated model of a vessel.

FIG. 32 illustrates a third-person view 420 of a generated model of a vessel. The generated model can be constructed using any of the imaging modalities described above, and includes a model of a vessel 415 viewed from a third-person. From this view, a physician can navigate a clot removal instrument from a current location to an occlusion site. The third-person view 420 shows a virtual, generated model of a catheter 400 as it is being driven into a virtual, generated model of vessel 415. The ring indicator including the right marker 417 and left marker 419 is also shown herein.

Advantageously, a clinician or physician can switch between any of the different views, such as the first-person view 410 and third-person view 420. In some embodiments, a picture-in-picture view can be displayed on a viewing screen in which a first-person view 410 is provided within a third-person view 420, or vice versa. Other possible views that can be generated besides a first-person view and a third-person view include zoomed-out and isometric views, all of which may be helpful at various points in a procedure.

A clinician or physician can use one or more of the generated models described above to navigate an instrument through a vessel to manipulate or remove a clot. Following initial access (e.g., through an incision), a physician can navigate and follow a predetermined path to a site of occlusion using pre-procedural and intra-procedural imaging. Live navigation data can be provided to the physician during a procedure to better navigate a tortuous path of the vessels. The live navigation data can be used to create a view or display as shown in FIGS. 31 and 32.

Before and during navigation, data can be collected to generate a "navigation model" and a "localization model." A navigation model is a collection of data that can be used to guide a physician to a site of occlusion. This model can include position coordinates of an occlusion, or a complex 3-D reconstruction of vascular anatomy, blood flow rates, occlusion size and composition, and optimal path to access an occlusion site. A localization model is a collection of data that can be used to determine the location of an instrument within a vessel. This model can be generated using information gathered from, for example, various sensors (e.g., EM or ultrasound) and/or shape sensing technology.

The images shown above, including the 3-D reconstruction in FIG. 30A, the first person view in FIG. 31 and the third person view in FIG. 32, can all be considered navigation models available to a clinician or physician. Such navigation models can be available to a physician during a clot removal procedure. During such a procedure, intra-procedure localization data can be collected. This localization data can be collected via electromagnetic sensing, shape-sensing technology, or image analysis based of fluoroscopic images. In embodiments involving robotic control, motor output and position, force, and torque sensing may also be inputs to the localization system.

Once localization of an instrument within a vessel has been established, the collected localization information may be reconciled with pre-procedural images. In some embodiments, the reconciliation is performed using a registration step. In some embodiments, registration can involve moving an instrument to one or more predetermined positions on/in a patient, or placing electromagnetic patches on specific parts of a patient. In some embodiments, data from CT and fluoroscopic imaging can be collected both prior to and during a procedure, and intra-procedure images can be registered to pre-procedure images.

In some embodiments, intra-procedure imaging can be used to improve the navigation model. For example, in some embodiments, intra-procedure imaging techniques can include fluoroscopy or intravascular ultrasound (IVUS). In some embodiments, IVUS in particular may enable concentric viewing a vascular lumen, thereby enabling a first person endoluminal camera view.

Figure 33A:
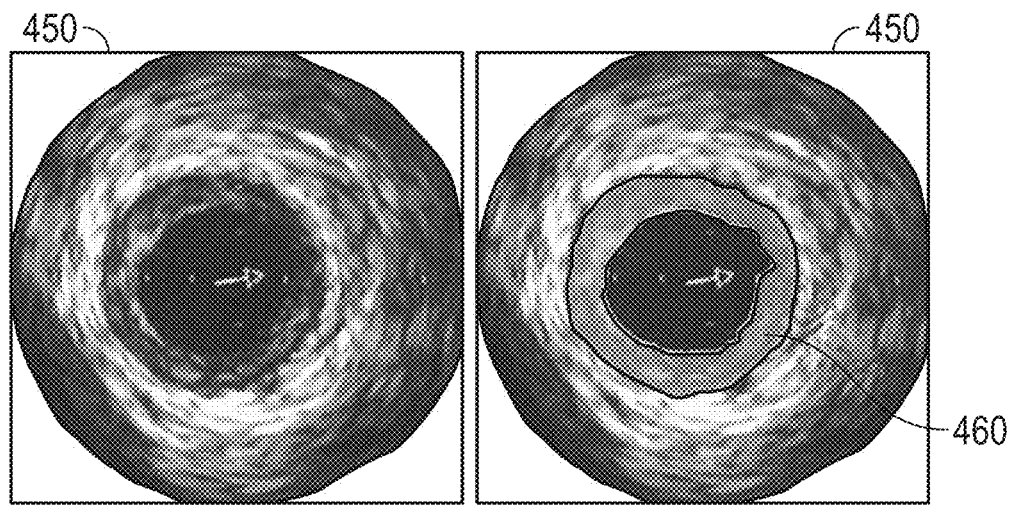
FIG. 33A illustrates two side-by-side concentric views to assist in navigation.

FIG. 33A illustrates two side-by-side concentric views generated by IVUS to assist in navigation. The first concentric view 450 on the left shows a concentric image of a vessel to be navigated. The second concentric view 450 on the right shows the same concentric image of a vessel, but with an optional virtual image overlay 460 positioned thereover. The optional virtual image overlay 460 advantageously identifies areas of stenosis and plaque that can be useful to a clinician or physician that is navigating through a vessel. Such an overlay 460 may better an enable an operator to navigate tortuous sections of vasculature to avoid regions of stenosis on the vessel walls.

Figure 33B:
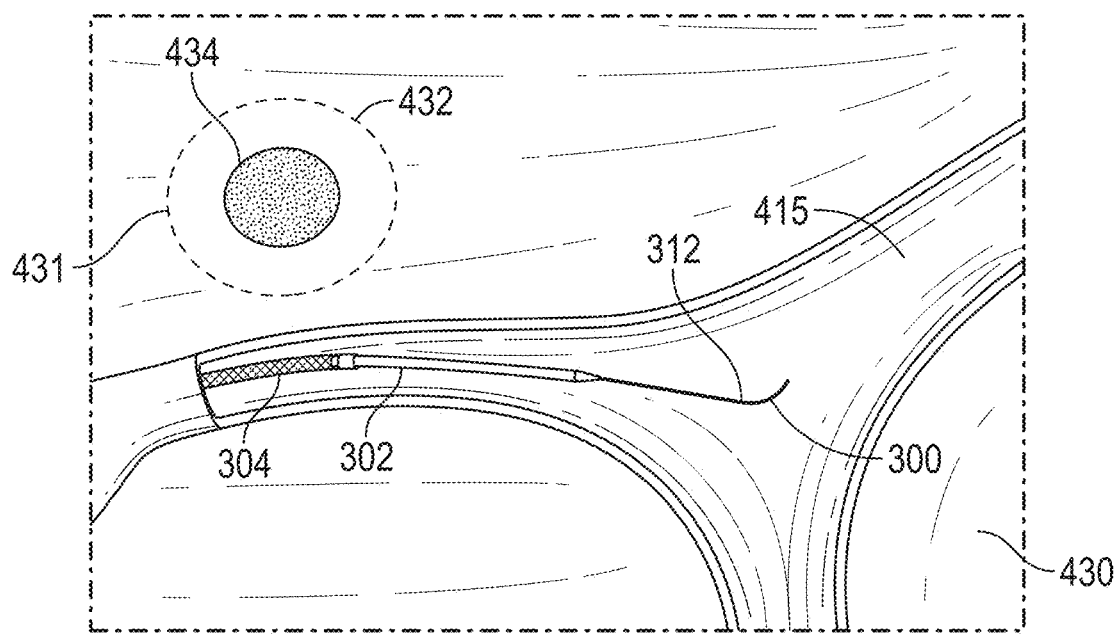
FIG. 33B illustrates a generated model accompanied by an indicator for catheter concentricity within a vessel.

FIG. 33B illustrates a generated model accompanied by an indicator 431 for catheter concentricity within a vessel. In this embodiment, a third person view 430 of a model vessel 415 (e.g., generated from any of the pre-procedural or intra-procedural imaging techniques described above) including a catheter instrument 300 for clot removal is shown therein. The catheter instrument 300 comprises the access sheath 304, clot removal catheter 302 (e.g., aspiration catheter), and clot disruptor 312. A virtual indicator overlay 431 overlays the third person view 430. The indicator 431 shows a representation of a vessel wall 432 and a representation of a tip of the catheter instrument 434. In some embodiments, the indicator 431 can be generated via one or more sensors positioned on or within the catheter instrument, as described above. Advantageously, the indicator 431 helps a clinician or physician to ensure that the driven catheter instrument 300 is concentric within a vessel 415, thereby reducing the risk of inadvertent vessel scraping and intra-operative strokes. While in the present embodiment, a virtual indicator 431 is overlay on top of a generated third person view of a vessel, in other embodiments, a virtual indicator 431 is overlay on top of a live or camera image of a vessel.

D. Methods for Clot Removal.

The systems and devices described above can be used to modify and remove clots. Below are some exemplary methods for performing clot modification and removal. These methods can be performed after performing pre-operational and/or intra-operational imaging on a patient's vasculature. As discussed above, in some embodiments, a virtual model or representation of the patient's vasculature can be generated based on the pre-operational and/or intra-operational imaging. The virtual model of the vasculature can then be displayed on a viewing screen for a physician. Upon registration of a catheter instrument for clot removal, a virtual model or representation of the catheter instrument can then be displayed on the virtual model of the vasculature. A clinician or physician can then use a controller (e.g., pendant, gimbal, or joystick) of a robotic system to drive the catheter instrument through the vasculature, using any of the steps or sequences described below.

Figure 34:
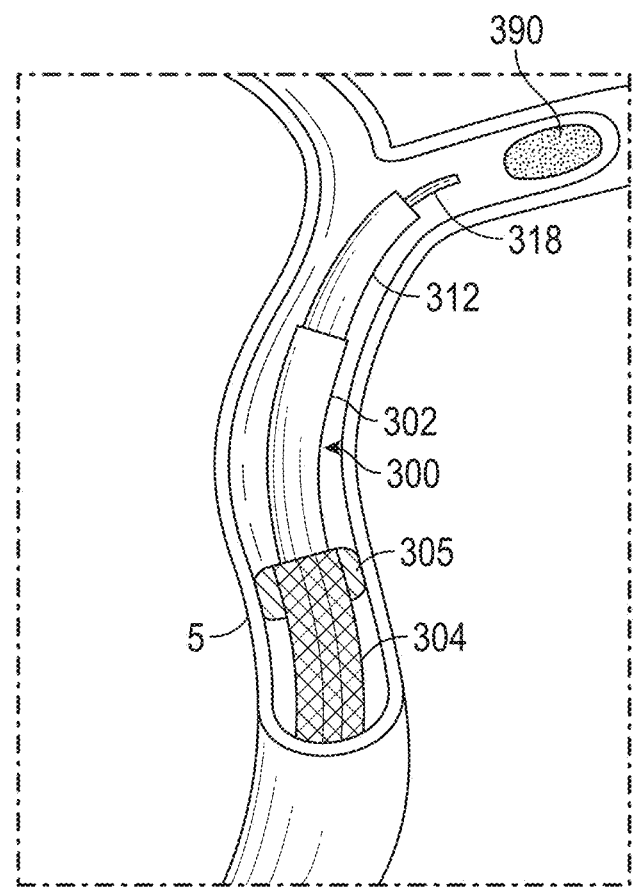
FIG. 34 illustrates a catheter instrument approaching a clot.
Figure 35:
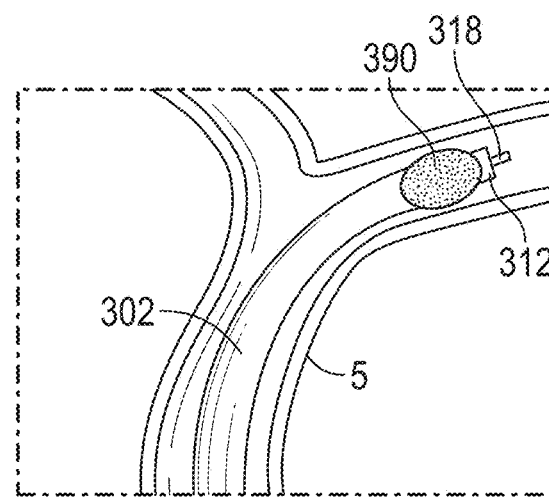
FIG. 35 illustrates the catheter instrument of FIG. 34 suctioning the clot.
Figure 36:
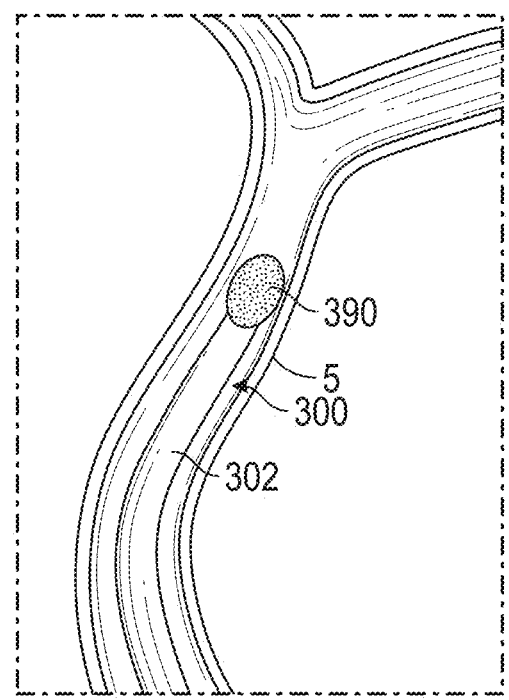
FIG. 36 illustrates the catheter instrument of FIG. 34 being retracted from a vessel after suctioning the clot.

FIGS. 34-36 illustrate a sequence of steps for clot modification and removal. In the present embodiment, a catheter instrument 300 including a clot removal catheter 302 in the form of an aspiration catheter is provided to suction and remove a clot. In other embodiments, the clot removal catheter 302 can deploy a 3-D structure such as a stent, net, basket or retriever to assist with clot removal. In some embodiments, the clot removal instrument 302 can both aspirate and deploy a 3-D structure.

FIG. 34 illustrates the delivery of a catheter instrument 300 to a position near a clot 390. The catheter instrument 300 comprises an access sheath 304, a clot removal catheter 302, a clot disruptor 312, and a guidewire 318. In some embodiments, the guidewire 318 (which is optional) can be delivered first through a vessel (e.g., via a femoral or radial incision) to a location adjacent the clot 390. The guidewire 318 can be delivered manually and/or robotically to a desired location. In other embodiments, other elongate members, such as the access sheath 304, can be delivered first through an incision, and the guidewire 318 can be delivered thereafter.

In the present embodiment, an access sheath 304 can be inserted into a patient, either before or after insertion of the guidewire 318. The access sheath 304 can be navigated and parked anywhere in the vasculature of a patient, such as at or near the carotid artery. In some embodiments, an inflatable member (e.g., balloon) 305 of the access sheath 304 can be deployed to assist in the stabilization of the access sheath 304 within a vessel 5. The access sheath 304 can be delivered manually and/or robotically to a desired location. The access sheath 304 can move in tandem and/or independently with the clot removal catheter 302.

The clot removal catheter 302 can be delivered through a lumen of the access sheath 304 and over the guidewire 318. In some embodiments, the clot removal catheter 302 can move in a telescoping fashion relative to the access sheath 304. While in the present embodiment, the clot removal catheter 302 comprises an aspiration catheter, in other embodiments, the clot removal catheter 302 can comprise a deployable 3-D structure (e.g., stent, net or basket), or a combination of an aspirator and deployable 3-D structure for clot capture. The clot removal catheter 302 can be delivered manually and/or robotically to a desired location. Advantageously, the clot removal catheter 302 can be of a smaller diameter than the access sheath 304, such that it can navigate even smaller vessels (e.g., beyond the carotid artery). Accordingly, in some embodiments, the clot removal catheter 302 can be positioned more distal than the access sheath 304 and closer to the clot 390 in some embodiments.

With the access sheath 304 and clot removal catheter 302 in place, a clot disruptor 312 can be inserted therethrough. Like the guidewire 318, the clot disruptor 312 is optional. In some embodiments, the clot disruptor 312 comprises an elongate member that is capable of modifying the size and shape of the clot 390.

In FIG. 34, the access sheath 304, clot removal catheter 302, clot disruptor 312, and guidewire 318 have been navigated through a vessel 5 to a location adjacent the clot 390.

FIG. 35 illustrates the catheter instrument 300 of FIG. 34 suctioning the clot 390. At this time, the clot disruptor 312, including the optional guide wire 314 therein, have pierced the clot 390. The clot removal catheter 302 has been positioned adjacent the clot 390 such that it is capable of suctioning the clot 390. A vacuum pump can be turned on, thereby generating suction energy in the clot removal catheter 302 to suction the clot 390.

FIG. 36 illustrates the catheter instrument 300 of FIG. 34 being retracted from a vessel 5 after suctioning the clot 390. At this time, the clot 390 has been suctioned by the clot removal catheter 302, and the entire catheter instrument 300 is being retracted through the vasculature of the patient.

Figure 37:
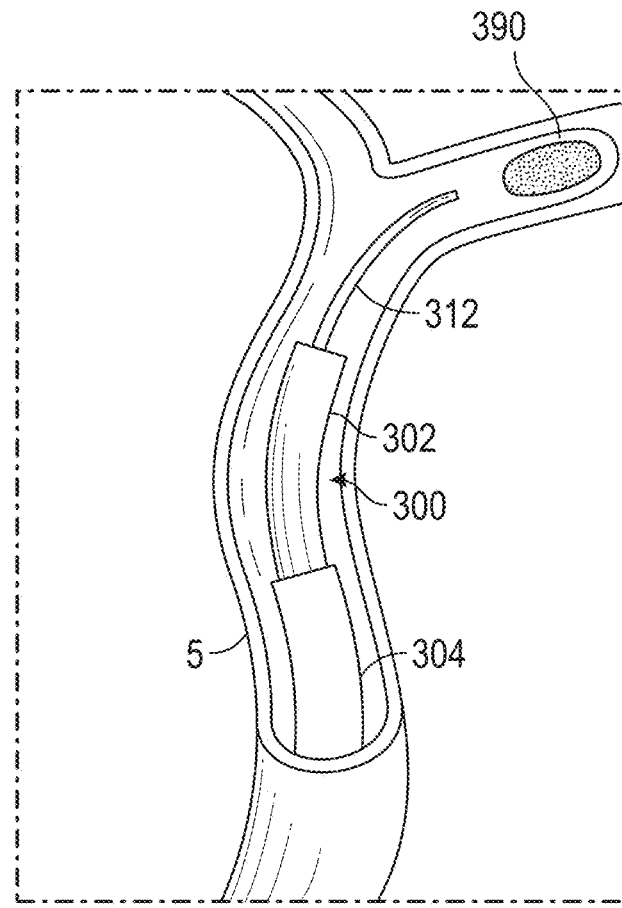
FIG. 37 illustrates an alternative catheter instrument approaching a clot.
Figure 38:
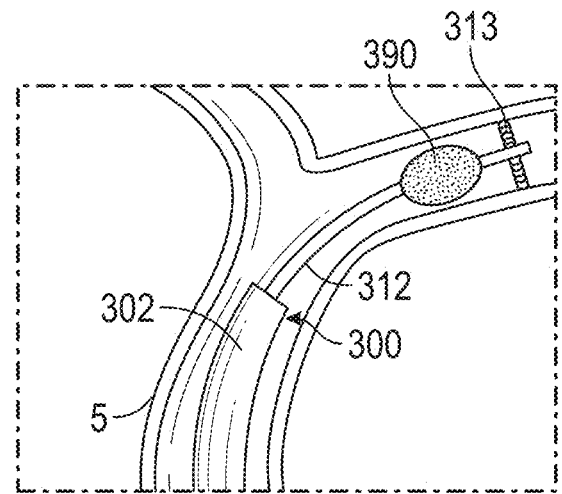
FIG. 38 illustrates the catheter instrument of FIG. 37 deploying a distal guard in a position distal of the clot.
Figure 39:
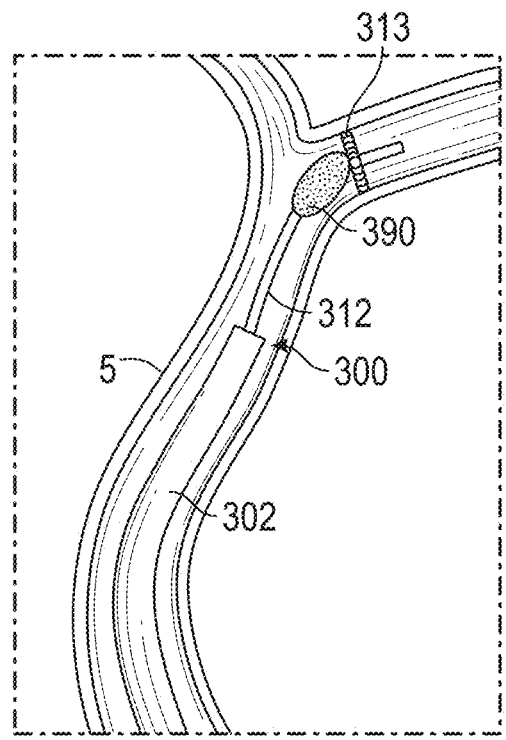
FIG. 39 illustrates the catheter instrument of FIG. 37 being retracted from a vessel after capturing the clot in the distal guard.

FIGS. 37-39 illustrate an alternative sequence of steps for clot modification and removal using a catheter instrument 300 that is different from that shown in FIGS. 34-36. In the present embodiment, a catheter instrument 300 such as shown in FIG. 29B is used for clot removal.

FIG. 37 illustrates the delivery of a catheter instrument 300 to a position near a clot 390. The catheter instrument 300 comprises an access sheath 304, a clot removal catheter 302, and a clot disruptor 312. In some embodiments, an optional guidewire (not shown) can be delivered first through a vessel (e.g., via a femoral or radial incision) to a location adjacent the clot 390. The guidewire can be delivered manually and/or robotically to a desired location. In other embodiments, other elongate members, such as the access sheath 304, can be delivered first through an incision, and the guidewire can be delivered thereafter.

In the present embodiment, an access sheath 304 can be inserted into a patient, either before or after insertion of the guidewire. The access sheath 304 can be navigated and parked anywhere in the vasculature of a patient, such as at or near the carotid artery. The access sheath 304 can be delivered manually and/or robotically to a desired location. The access sheath 304 can move in tandem and/or independently with the clot removal catheter 302.

The clot removal catheter 302 can be delivered through a lumen of the access sheath 304 and over the guidewire 318. In some embodiments, the clot removal catheter 302 can move in a telescoping fashion relative to the access sheath 304. While in the present embodiment, the clot removal catheter 302 comprises an aspiration catheter, in other embodiments, the clot removal catheter 302 can comprise a deployable 3-D structure (e.g., stent, net or basket), or a combination of an aspirator and deployable 3-D structure for clot capture. The clot removal catheter 302 can be delivered manually and/or robotically to a desired location. Advantageously, the clot removal catheter 302 can be of a smaller diameter than the access sheath 304, such that it can navigate even smaller vessels (e.g., beyond the carotid artery). Accordingly, in some embodiments, the clot removal catheter 302 can be positioned more distal than the access sheath 304 and closer to the clot 390 in some embodiments.

With the access sheath 304 and clot removal catheter 302 in place, a clot disruptor 312 can be inserted therethrough. In some embodiments, the clot disruptor 312 comprises an elongate member that is capable of modifying the size and shape of the clot 390. In the present embodiment, the clot disruptor 312 comprises a multi-functional distal guard 313 (shown in FIGS. 38 and 39) that has yet to be deployed.

FIG. 38 illustrates the catheter instrument 300 of FIG. 37 after deploying a distal guard 313 in a position distal of the clot 390. At this time, the clot disruptor 312 has pierced the clot 390. A distal guard 313 has been deployed along the clot disruptor 312 in a distal location from the clot 390. The distal guard 313 advantageously serves to block embolic material from the clot 390 that may inadvertently drift into the vessel 5, thereby reducing the risk of a downstream stroke. Advantageously, the distal guard 313 can work in conjunction with the aspirator of the clot removal catheter 302 to remove the clot 390. As shown in FIG. 39, the distal guard 313 is multi-functional in that it also helps to physically retract and remove the clot 390 from the vasculature. Advantageously, either before, during or after the clot disruptor 312 has pierced the clot 390, the vacuum pump can be turned on to provide for aspiration from the clot removal catheter 302. For example, advantageously, in some embodiments, the suctioning capabilities of the clot removal catheter 302 can be turned on during the piercing of the clot 390 by the clot disruptor 312 so that it can help to prevent movement of the clot 390 while it is being pierced. This is beneficial as any contact with the clot 390 (e.g., via the clot disruptor 312) can cause the clot 390 and smaller particles of the clot to drift to undesirable locations. As such, applying suction from the clot removal catheter 302 before, during, or after piercing of the clot can provide a number of advantages.

FIG. 39 illustrates the catheter instrument 300 of FIG. 37 being retracted from a vessel 5 after capturing the clot 390 in the distal guard 313. As the catheter instrument 300 is retracted, the distal guard 313 physically retracts the clot 390 from the vessel 5. In some embodiments, during the retraction, the clot removal catheter 302 is also in the process of aspiration. By providing aspiration, this advantageously reduces the risk of the clot 390 drifting inadvertently into adjacent vessels of the patient, thereby reducing the risk of downstream strokes.

While FIGS. 34-36 and 37-39 illustrate sequences of particular methods of clot removal, one skilled in the art will appreciate that the sequences are exemplary, and that the systems and methods described herein are not limited to such procedures.

Figure 40:
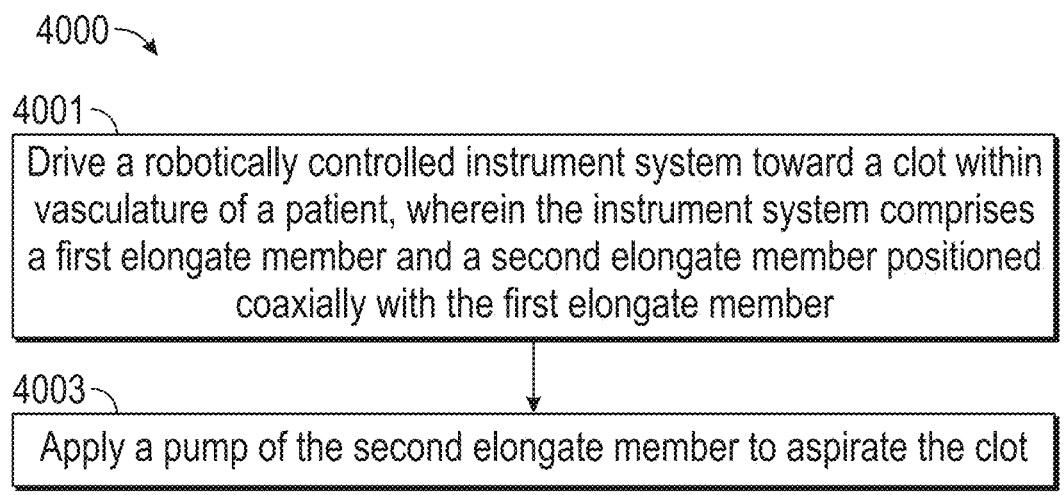
FIG. 40 is a flowchart illustrating an example method of clot removal.

FIG. 40 is a flowchart illustrating an example method 4000 for clot removal. The method 4000 can be implemented in certain robotic systems, such as the robotic systems illustrated in FIGS. 1-15 and 21 and others. In some implementations, one or more computer devices may be configured to execute the method 4000. The computer devices may be embodied by one or more processors (such as that represented by 240 in FIG. 21) that can be used to execute the method 4000. The computer-readable memory may store instructions that may be executed by the processor(s) to perform the method 4000. The instructions may include one or more software modules as described more below. By way of example and not limitation, the computer devices may be in the tower 30 shown in FIG. 1, the cart shown in FIGS. 1-4, 21, and 42, the beds shown in FIGS. 5-10, 21, and 41-43, etc. As described previously, certain parts of the robotically controlled instrument system 300 may be robotically or manually controlled.

The method 4000 begins at block 4001, at which a robotically controlled instrument system 300 is driven toward a clot 390 within vasculature 5 of a patient. The robotically controlled system 300 may include at least the first elongate member 304 and the second elongate member 302 positioned coaxially with the first elongate member 304. The robotically controlled instrument system 300 may include additional elongate members and other features, as described previously. The first elongate member 304 may be an access sheath and the second elongate member 302 may be a clot removing (e.g., aspiration) catheter.

At block 4003, the method 4000 involves applying a pump of the second elongate member 302 to aspirate the clot 390. As described previously, a vacuum pump can be turned on, thereby generating suction energy in the clot removal catheter 302 to suction the clot 390.

E. Software.

Various aspects of the systems, devices and methods described above can be robotically controlled. Advantageously, one or more processors (such as that represented by 240 in FIG. 21) can be used to assist in the imaging, driving and navigation of the systems and devices described above.

In related aspects, the one or more processors may be implemented as any of a variety of suitable circuitry, such as one or more microprocessors, application specific integrated circuits (ASICs), field programmable gate arrays (FPGAs), discrete logic, software, hardware, firmware or any combination thereof. When the techniques are implemented partially in software, a device may store instructions for the software in a suitable, non-transitory computer-readable medium and execute the instructions in hardware using one or more processors to perform the techniques of this disclosure.

In some embodiments, one or more processors can be used to prioritize cases of complex or multi-vessel occlusion. This can be important, for example, in the event that there multiple sites of occlusion due to multiple clots. In some embodiments, the processors can be used to identify sites of lesser perfusion due to clotting using pre-operational images, such as CT and CTA. In other embodiments, in addition to using pre-operational images, one or more processors can be used to prioritize cases of complex or multi-vessel occlusion based on information related to clot size, flow or perfusion, and blockage location. Such sites of lesser perfusion can be identified to a physician, who can then prioritize treatment. In some embodiments, upon identifying a site of lesser perfusion, a physician can manually move a clot removing instrument from one location to another to address the site of lesser perfusion. In other embodiments, a clot removing instrument can be automatically moved from one location to another, with little to no input from a physician.

In some embodiments, one or more processors can also assist in navigation. As noted above, a navigation model can be provided that includes a virtual representation of relevant vasculature. Image processing and computer vision algorithms can be used to identify the site of an occlusion, quantify the size and severity of the blockage, and evaluate perfusion. In some embodiments, a path can be generated anywhere along an access site (e.g., femoral or radial) to the site of the occlusion, either before or during a procedure. The path can be generated on a viewing screen for a clinician or physician. Advantageously, as a physician drives a catheter instrument including a clot removal catheter towards the clot, the location of the catheter instrument along the path can be updated. The location can be updated with the help of various types of technology, including EM and ultrasound sensors, as well as fiber optic shape sensing technology. In some embodiments, the processor can be regularly updated with localization information until a surgeon completes a clot removing procedure. In some embodiments, the path that the catheter instrument took can be recorded and stored on a computer-readable medium. In some embodiments, this information can help a catheter instrument to be more easily retracted from the vasculature.

3. Implementing Systems and Terminology.

Implementations disclosed herein provide systems, devices and methods for the modification and removal of clots. One skilled in the art will appreciate that any of the systems described above can be used to drive any of the instruments to perform any of the methods described above.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Any parameters related to robotic motion, imaging and navigation, and task prioritization as described above, may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotically controlled system for removing a clot from a patient comprising:
   an instrument system including:
      a first elongate member;
      a second elongate member positioned coaxially with the first elongate member,
         wherein the second elongate member includes at least one articulation cable and is coupled to a pump for performing an aspiration function on the clot,
         wherein the first and second elongate members each have at least one articulation cable for bending the respective one of the first or second elongate members,
         wherein the first elongate member has a greater number of articulation cables than the second elongate member, and wherein the first elongate member is capable of being articulated independently from the second elongate member; and
a third elongate member that is positioned within the first elongate member and the second elongate member, wherein the third elongate member comprises:
a blunt distal tip configured to pierce the clot;
a clot cutter configured to reduce the clot to smaller particles; and
a distal guard configured to be robotically deployed distal to the clot to prevent the smaller particles of the clot from being distributed downstream in the patient;
and
a retriever coupled to the second elongate member and configured to capture the clot and the smaller particles of the clot; and
an instrument drive system for driving the instrument system, wherein the instrument drive system comprises a first instrument driver for driving the first elongate member and a second instrument driver for driving the second elongate member.

2. The robotically controlled system of claim 1, wherein the third elongate member is capable of physically modifying the clot.

3. The robotically controlled system of claim 2, wherein the blunt distal tip comprises a blade.

4. The robotically controlled system of claim 1, further comprising a fourth elongate member positioned within the third elongate member.

5. The robotically controlled system of claim 4, wherein the fourth elongate member comprises a guidewire.

6. The robotically controlled system of claim 1, wherein the first elongate member comprises an inflatable member for occluding a vessel.

7. The robotically controlled system of claim 1, further comprising a processor system for assisting in task prioritization.

8. The robotically controlled system of claim 7, wherein the processor system is capable of gathering information related to one or more of a location of an occlusion and/or a severity of blockage by the clot.

9. A robotically controlled system comprising:
an instrument system including:
a first elongate member;
a second elongate member;
wherein the first elongate member and the second elongate member each have at least one articulation cable for bending the respective one of the first or second elongate members,
wherein the first elongate member has a greater number of articulation cables than the second elongate member,
wherein the first elongate member is capable of being articulated independently from the second elongate member,
wherein the second elongate member is positioned coaxially with the first elongate member,
a third elongate member that is positioned within the first elongate member and the second elongate member, wherein the third elongate member comprises:
a blunt distal tip configured to pierce a clot;
a clot cutter configured to reduce the clot to smaller particles; and
a distal guard configured to be robotically deployed distal to the clot to prevent the smaller particles of the clot from being distributed downstream in a patient; and
a retriever coupled to the second elongate member and configured to capture the clot and the smaller particles of the clot; and
an instrument drive system for driving the instrument system, wherein the instrument drive system comprises a first instrument driver for driving the first elongate member and a second instrument driver for driving the second elongate member.

10. The robotically controlled system of claim 9, wherein the instrument system is coupled to a pump for performing an aspiration function to remove the clot from the patient.

11. The robotically controlled system of claim 9, wherein the third elongate member is capable of physically modifying the clot in the patient.

12. The robotically controlled system of claim 11, wherein the blunt distal tip comprises a blade.

13. The robotically controlled system of claim 11, further comprising a fourth elongate member positioned within the third elongate member.

14. The robotically controlled system of claim 13, wherein the fourth elongate member comprises a guidewire.

15. The robotically controlled system of claim 11, wherein the first elongate member comprises an inflatable member for occluding a vessel.

16. The robotically controlled system of claim 11, further comprising a processor system for assisting in task prioritization.

17. The robotically controlled system of claim 1, wherein the first elongate member comprises at least one coil pipe, wherein the at least one coil pipe receives the respective at least one articulation cable.

18. The robotically controlled system of claim 9, wherein the first elongate member comprises at least one coil pipe, wherein the at least one coil pipe receives the respective at least one articulation cable.

\* \* \* \* \*